United States Patent
Naik et al.

(10) Patent No.: US 10,285,973 B2
(45) Date of Patent: May 14, 2019

(54) SGLT-2 INHIBITORS FOR TREATING METABOLIC DISORDERS IN PATIENTS WITH RENAL IMPAIRMENT OR CHRONIC KIDNEY DISEASE

(71) Applicants: Merck Sharp & Dohme Corp., Rahway, NJ (US); Pfizer Inc., New York, NY (US)

(72) Inventors: Ramachandra G. Naik, Short Hills, NJ (US); Elizabeth S. Ommen, Dobbs Ferry, NY (US); James Michael Rusnak, New York, NY (US); Steven G. Terra, New York, NY (US)

(73) Assignees: Merck Sharp & Dohme Corp., Rahway, NJ (US); Pfizer Inc., New York, NY (US)

( * ) Notice: Subject to any disclaimer, the term of this patent is extended or adjusted under 35 U.S.C. 154(b) by 0 days.

(21) Appl. No.: 15/523,512

(22) PCT Filed: Nov. 5, 2015

(86) PCT No.: PCT/US2015/059122
§ 371 (c)(1),
(2) Date: May 1, 2017

(87) PCT Pub. No.: WO2016/077126
PCT Pub. Date: May 19, 2016

(65) Prior Publication Data
US 2017/0304262 A1 Oct. 26, 2017

Related U.S. Application Data

(60) Provisional application No. 62/077,555, filed on Nov. 10, 2014, provisional application No. 62/139,211, filed on Mar. 27, 2015.

(51) Int. Cl.
| | | |
|---|---|---|
| *A61K 31/357* | (2006.01) | |
| *A61K 31/35* | (2006.01) | |
| *A61K 31/155* | (2006.01) | |
| *A61K 31/4985* | (2006.01) | |
| *A61P 3/10* | (2006.01) | |

(52) U.S. Cl.
CPC .......... *A61K 31/357* (2013.01); *A61K 31/155* (2013.01); *A61K 31/35* (2013.01); *A61K 31/4985* (2013.01); *A61P 3/10* (2018.01)

(58) Field of Classification Search
CPC ................ A61K 31/155; A61K 31/357; A61K 31/4985; A61K 31/35; A61P 3/10
See application file for complete search history.

(56) References Cited

U.S. PATENT DOCUMENTS

| | | | |
|---|---|---|---|
| 8,080,580 B2 | 12/2011 | Mascitti et al. | |
| 8,143,217 B2 * | 3/2012 | Balkan ................. | A61K 31/155 514/6.9 |
| 2011/0046076 A1 | 2/2011 | Eickelmann et al. | |
| 2013/0137646 A1 * | 5/2013 | Wienrich .......... | A61K 31/4515 514/23 |
| 2014/0303098 A1 | 10/2014 | Broedl et al. | |
| 2014/0315832 A1 | 10/2014 | Broedl et al. | |

FOREIGN PATENT DOCUMENTS

WO WO-2010023594 A1 * 3/2010 ........... C07D 493/08

OTHER PUBLICATIONS

Levey et. al., Lancet, 2011, Little Brown & Co., vol. 379, pp. 165-180 (Year: 2011).*
AstraZeneca, Forxiga, INN-dapagliflozin prescribing information, 2014, pp. 1-30 (Year: 2014).*
Clinicaltrials, A Study of the Efficacy and Safety of Ertugliflozin in Participants With Type 2 Diabetes Mellitus With Stage 3 Chronic Kidney Disease Who Have Inadequate Glycemic Control on Antihyperglycemic Therapy (MK-8835-001), ClinicalTrials, 2013, p. 1-5.
Harada, S. et al., Neuroprotective effect through the cerebral sodium-glucose transporter on the development of ischemic damage in global ischemia, Elsevier, 2013, p. 61-68, 1541.
White, J. R. et al., Apple Trees to Sodium Glucose Co-Transporter Inhibitors: A Review of SGLT2 Inhibition, Clinical Diabetes, 2010, p. 5-10, vol. 28, No. 1.
Andre J. Screen, Pharmacokinetics, Pharmacodynamics and Clinical Use of SGLT2 Inhibitors in Patients with Type 2 Diabetes Mellitus and Chronic Kidney Disease, Springer International Publishing Switzerland, 2015, 691-708.
German Ramirez et al., Clinical Practice Considerations and review of the Literature for the use of DPP-4 Inhibitors in Patients with Type 2 Diabetes and Chronic Kidney Disease, Endocrine Practice, 2013, pp. 1025-1034, 19.
Segluromet Prescribing Information, 2017, pp. 1-31.

* cited by examiner

*Primary Examiner* — Sarah Pihonak
(74) *Attorney, Agent, or Firm* — Janet E. Fair; Catherine D. Fitch

(57) ABSTRACT

The present invention relates to certain SGLT-2 inhibitors, such as ertugliflozin or a co-crystal or a pharmaceutically acceptable salt thereof, for treating and/or preventing metabolic disorders, such as type 1 or type 2 diabetes mellitus or pre-diabetes, in patients with renal impairment or chronic kidney disease (CKD). The present invention also relates to methods for preventing neuronal damage following the incidence of ischemic stroke and close-head traumatic brain injury in animals comprising the step of administering to an animal, in need of such treatment, a therapeutically effective amount of ertugliflozin or a co-crystal or a pharmaceutically acceptable salt thereof.

13 Claims, No Drawings

SGLT-2 INHIBITORS FOR TREATING METABOLIC DISORDERS IN PATIENTS WITH RENAL IMPAIRMENT OR CHRONIC KIDNEY DISEASE

CROSS-REFERENCE TO RELATED APPLICATIONS

This application is a U.S. National Phase application under 35 U.S.C. § 371 of PCT Application No. PCT/US15/059122, filed Nov. 5, 2015, which published as WO2016/077126 A1 on May 19, 2016, and claims priority under 35 U.S.C. § 365(b) from U.S. provisional patent application No. 62/139,211, filed Mar. 27, 2015 and U.S. provisional patent application No. 62/077,555, filed Nov. 10, 2014.

FIELD OF THE INVENTION

The present invention relates to certain SGLT-2 inhibitors, such as ertugliflozin or a co-crystal or a pharmaceutically acceptable salt thereof, for treating and/or preventing metabolic disorders, such as type 2 or type 1 diabetes mellitus or pre-diabetes, in patients with renal impairment or chronic kidney disease (CDK).

BACKGROUND

Recently, sodium-glucose co-transport (SGLT) inhibitors have been found to be effective in treating prediabetes, type 1 or type 2 diabetes mellitus. Particularly SGLT2 inhibitors have been shown to block the reabsorption of glucose from the renal filtrate in the glomerulus thereby inducing glucose excretion in the urine. As excess glucose is excreted, there is a decrease in blood glucose level, decreased hepatic storage of glucose, decreased insulin secretion and, subsequently, decreased carbohydrate conversion to fat and, ultimately, reduced accumulated fat. Selective inhibition of SGLT2 is expected to normalize plasma glucose by enhancing glucose excretion. Consequently, SGLT2 inhibitors provide an attractive means for the improvement of diabetic conditions without increasing body weight or the risk of hypoglycemia. See, Isaji, M., *Current Opinion Investigational Drugs*, 8(4), 285-292 (2007). For a general review of SGLT as a therapeutic target, see also Asano, T., et al., *Drugs of the Future*, 29(5), 461-466 (2004).

Nephropathy is a well-established complication of poor glycemic control in patients with diabetes. An estimated 10-36% of patients with type 2 diabetes mellitus (T2DM) have some degree of renal impairment and chronic kidney disease (CKD) is present in approximately 40% of patients with diabetes. CKD has been classified into 5 stages, where stage 1 is kidney damage with normal GFR (mL/min/1.73 m$^2$) of 90; stage 2 is kidney damage with a mild decrease in glomerular filtration rate (GFR) (GFR 60-89); stage 3 is a moderate decrease in GFR (GFR 30-59); stage 4 is a severe decrease in GFR (GFR 15-29); and stage 5 is kidney failure (GFR<15 or dialysis). The use of a number of anti-diabetes agents is restricted in patients with renal impairment. Therefore, there is a need for methods, medicaments and pharmaceutical compositions for the treatment of metabolic disorders, such as type 2 diabetes, in patients with renal impairment or chronic kidney disease (CDK).

Additionally, SGLT plays a role at the blood brain barrier in the blood-to-brain transport of glucose during ischemic conditions, and inhibition of SGLT during stroke has the potential to improve stroke outcomes (Vemula et al., A Functional Role for Sodium-Dependent Glucose Transport across the Blood-Brain Barrier during Oxygen Glucose Deprivation, The Journal of Pharmacology and Experimental Therapeutics, Vol. 328:487-495, 2009). Studies have also shown that post-ischemic hyperglycemia exacerbates the development of cerebral ischemic neuronal damage through the cerebral sodium-glucose transporter, and that neuronal damage following hyperglycemia was not observed following administration of phlorizin, an SGLT1 and SGLT2 inhibitor (Yamazaki et al., Post-ischemic hyperglycemia exacerbates the development of cerebral ischemic neuronal damage through the cerebral sodium-glucose transporter, Brain Research 1489:113-120, 2012). Thus, SGLT-2 inhibitors could be useful for reducing neuronal damage following the incidence of ischemic stroke and close-head traumatic brain injury. Therefore, there is a need for methods, medicaments and pharmaceutical compositions for use in the reduction of neuronal damage following the incidence of ischemic stroke and close-head traumatic brain injury.

SUMMARY

The present invention relates to certain SGLT-2 inhibitors for treating and/or preventing metabolic disorders, such as type 2 diabetes mellitus, in patients with renal impairment or chronic kidney disease (CDK).

Additionally, the present invention relates to certain SGLT-2 inhibitors preventing neuronal damage following the incidence of ischemic stroke and close-head traumatic brain injury in animals.

In certain embodiments, compounds of Formula (A) and Formula (B) have been found to act as sodium-glucose cotransport (SGLT) inhibitors, in particular, SGLT2 inhibitors and therefore, may be used in the treatment of diseases mediated by such inhibition (e.g., diseases related to obesity, Type 2 diabetes, and obesity-related and diabetes-related co-morbidities) in patients with renal impairment or chronic kidney disease (CDK). These compounds may be represented by Formulas (A) and (B) as shown below:

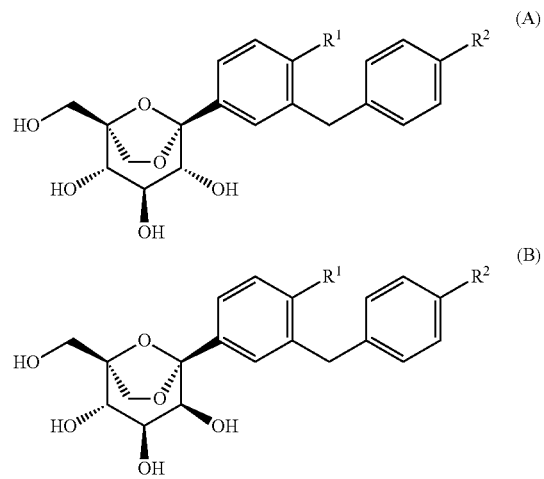

wherein R$^1$ is H, (C$_1$-C$_4$)alkyl, (C$_1$-C$_4$)alkoxy, Cl, F, cyano, fluoro-substituted (C$_1$-C$_2$)alkyl, (C$_1$-C$_4$)alkyl-SO$_2$—, or (C$_3$-C$_6$)cycloalkyl; and R$^2$ is (C$_1$-C$_4$)alkyl, (C$_1$-C$_4$)alkoxy, (C$_2$-C$_4$)alkynyl, 3-oxetanyloxy, 3-tetrahydrofuranyloxy, Cl, F, cyano, fluoro-substituted (C$_1$-C$_2$)alkyl, (C$_1$-C$_4$)alkyl-SO$_2$—, (C$_3$-C$_6$)cycloalkyl, or a (C$_5$-C$_6$)heterocycle having 1 for 2 heteroatoms each independently selected from N, O, or S.

It is generally understood by those skilled in the art that various substituents may be added to the compounds of Formula (A) or Formula (B) so long as the substituent(s) selected does not adversely affect the pharmacological characteristics of the compound or adversely interfere with the use of the medicament.

Specific compounds of Formula (A) include: (1S,2S,3S, 4R,5S)-1-hydroxymethyl-5-[3-(4-methoxy-benzyl)-4-methyl-phenyl]-6,8-dioxa-bicyclo[3.2.1]octane-2,3,4-triol; (1S,2S,3S,4R,5S)-5-[3-(4-ethoxy-benzyl)-4-methyl-phenyl]-1-hydroxymethyl-6,8-dioxa-bicyclo[3.2.1]octane-2,3, 4-triol; (1S,2S,3S,4R,5S)-5-[4-chloro-3-(4-methoxy-benzyl)-phenyl]-1-hydroxymethyl-6,8-dioxa-bicyclo[3.2.1] octane-2,3,4-triol; (1S,2S,3S,4R,5S)-5-[4-chloro-3-(4-ethoxy-benzyl)-phenyl]-1-hydroxymethyl-6,8-dioxa-bicyclo[3.2.1]octane-2,3,4-triol; (1S,2S,3S,4R,5S)-5-[4-fluoro-3-(4-methoxy-benzyl)-phenyl]-1-hydroxymethyl-6, 8-dioxa-bicyclo[3.2.1]octane-2,3,4-triol; 2-(4-methoxybenzyl)-4-((1S,2S,3S,4R,5S)-2,3,4-trihydroxy-1-(hydroxymethyl)-6,8-dioxa-bicyclo[3,2,1]oct-5-yl) benzonitrile; 2-(4-ethoxybenzyl)-4-((1S,2S,3S,4R,5S)-2,3, 4-trihydroxy-1-(hydroxymethyl)-6,8-dioxa-bicyclo[3,2,1] oct-5-yl)benzonitrile; (1S,2S,3S,4R,5S)-5-[3-(4-ethoxy-benzyl)-4-fluoro-phenyl]-1-hydroxymethyl-6,8-dioxa-bicyclo[3.2.1]octane-2,3,4-triol; (1S,2S,3S,4R,5S)-5-{4-fluoro-3-[4-(tetrahydro-furan-3-yloxy)-benzyl]-phenyl}-1-hydroxymethyl-6,8-dioxa-bicyclo[3.2.1]octane-2,3,4-triol; (1S,2S,3S,4R,5S)-5-[3-(4-chlorobenzyl)-4-fluorophenyl]-1-hydroxymethyl-6,8-dioxabicyclo[3.2.1]octane-2,3,4-triol; (1S,2S,3S,4R,5S)-5-{4-fluoro-3-[4-(oxetan-3-yloxy)-benzyl]-phenyl}-1-hydroxymethyl-6,8-dioxa-bicyclo[3.2.1]octane-2,3,4-triol; and (1S,2S,3S,4R,5S)-5-{4-chloro-3-[4-(oxetan-3-yloxy)-benzyl]-phenyl}-1-hydroxymethyl-6,8-dioxa-bicyclo[3.2.1]octane-2,3,4-triol.

Specific compounds of Formula (B) include: (1S,2S,3S, 4S,5S)-1-hydroxymethyl-5-[3-(4-methoxy-benzyl)-4-methyl-phenyl]-6,8-dioxa-bicyclo[3.2.1]octane-2,3,4-triol; (1S,2S,3S,4S,5S)-5-[3-(4-ethoxy-benzyl)-4-methyl-phenyl]-1-hydroxymethyl-6,8-dioxa-bicyclo[3.2.1]octane-2,3, 4-triol; (1S,2S,3S,4S,5S)-5-[4-chloro-3-(4-methoxy-benzyl)-phenyl]-1-hydroxymethyl-6,8-dioxa-bicyclo[3.2.1] octane-2,3,4-triol; (1S,2S,3S,4S,5S)-5-[4-chloro-3-(4-ethoxy-benzyl)-phenyl]-1-hydroxymethyl-6,8-dioxa-bicyclo[3.2.1]octane-2,3,4-triol; (1S,2S,3S,4S,5S)-5-[4-fluoro-3-(4-methoxy-benzyl)-phenyl]-1-hydroxymethyl-6, 8-dioxa-bicyclo[3.2.1]octane-2,3,4-triol; (1S,2S,3S,4S,5S)-5-[3-(4-ethoxy-benzyl)-4-fluoro-phenyl]-1-hydroxymethyl-6,8-dioxa-bicyclo[3.2.1]octane-2,3,4-triol; and (1S,2S,3S, 4S,5S)-5-[3-(4-chlorobenzyl)-4-fluorophenyl]-1-hydroxymethyl-6,8-dioxabicyclo[3.2.1]octane-2,3,4-triol.

An SGTL2 inhibitor used in the methods of the present invention is a compound having the formula (4A):

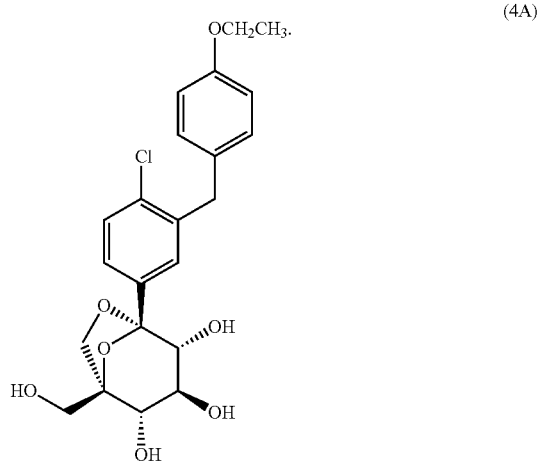 [SMILES: CCOc1ccc(Cc2cc([C@]34OC[C@](CO)(O3)[C@@H](O)[C@H](O)[C@H]4O)ccc2Cl)cc1]

(4A)

having the chemical name (1S,2S,3S,4R,5S)-5-[4chloro-3-(4-ethoxy-benzyl)-phenyl]-1-hydroxymethyl-6,8-dioxa-bicyclo[3.2.1]octane-2,3,4-triol and described in U.S. Pat. No. 8,080,580. The compound of 4(A) is further known as ertugliflozin.

One aspect of the present invention is a method for treating a disease, disorder, or condition modulated by SGLT2 inhibition in animals that includes the step of administering to an animal (preferably, a human) with renal impairment or chronic kidney disease (CDK), in need of such treatment a therapeutically effective amount of a compound of the present invention (or a pharmaceutical composition thereof). Diseases, conditions, and/or disorders modulated by SGLT2 inhibition include, e.g., type 2 diabetes, diabetic nephropathy, insulin resistance syndrome, hyperglycemia, hyperinsulinemia, hyperlipidemia, impaired glucose tolerance, obesity (including weight control or weight maintenance), hypertension, and reducing the level of blood glucose.

Additionally, another aspect of the present invention is directed to a method for preventing neuronal damage following the incidence of ischemic stroke and close-head traumatic brain injury in animals that includes the step of administering to an animal (preferably, a human) in need of such treatment a therapeutically effective amount of a compound of the present invention (or a pharmaceutical composition thereof).

In certain embodiments the present invention is directed to a method of treating prediabetes, type 1 or type 2 diabetes mellitus in a patient comprising administering ertugliflozin or a co-crystal or a pharmaceutically acceptable salt thereof to the patient, wherein the patient has moderate renal impairment or stage 3 chronic kidney disease (CKD). When used herein, the expression "ertugliflozin or a co-crystal or a pharmaceutically acceptable salt thereof" includes a pharmaceutically acceptable salt of ertugliflozin as well as, a pharmaceutically acceptable salt of the co-crystal of ertugliflozin. In certain embodiments, the patient has moderate renal impairment or stage 3A chronic kidney disease (CKD). In other embodiments, the patient has moderate B renal impairment or stage 3B chronic kidney disease (CKD).

In certain embodiments, ertugliflozin or a co-crystal or a pharmaceutically acceptable salt thereof is administered as a pharmaceutical composition. In certain embodiments, the pharmaceutical composition comprises 5 mg or 15 mg of ertugliflozin or a co-crystal or a pharmaceutically acceptable salt thereof. In certain embodiments, ertugliflozin or a co-crystal or a pharmaceutically acceptable salt thereof is administered once daily.

In other embodiments, the present invention is directed to a method for improving glycemic control in a patient with type 2 diabetes comprising administering ertugliflozin or a co-crystal or a pharmaceutically acceptable salt thereof to the patient, wherein the patient has moderate renal impairment or stage 3 chronic kidney disease (CKD). In certain embodiments, the patient has moderate renal impairment or stage 3A chronic kidney disease (CKD). In other embodiments, the patient has moderate B renal impairment or stage 3B chronic kidney disease (CKD). In certain embodiments, ertugliflozin or a co-crystal or a pharmaceutically acceptable salt thereof is administered as a pharmaceutical composition. In certain embodiments, the pharmaceutical composition comprises 5 mg or 15 mg of ertugliflozin or a co-crystal or a pharmaceutically acceptable salt thereof. In certain embodiments, ertugliflozin or a co-crystal or a pharmaceutically acceptable salt thereof is administered once daily.

In yet other embodiments, the present invention is direct to a method of treating prediabetes, type 1 or type 2 diabetes comprising: a) determining the estimated glomerular filtration rate (eGFR) of a patient in need of treatment for prediabetes, type 1 or type 2 diabetes; b) administering ertugliflozin or a co-crystal or a pharmaceutically acceptable salt thereof to the patient, if the eGFR of the patient is ≥30 ml/min/1.73 m². In certain embodiments, ertugliflozin or a co-crystal or a pharmaceutically acceptable salt thereof is administered if the eGFR of the patient is between ≥30 ml/min/1.73 m² and <60 ml/min/1.73 m². In certain embodiments, ertugliflozin or a co-crystal or a pharmaceutically acceptable salt thereof is administered if the eGFR of the patient is ≥45 ml/min/1.73 m². In certain embodiments, ertugliflozin or a co-crystal or a pharmaceutically acceptable salt thereof is administered if the eGFR of the patient is between ≥45 ml/min/1.73 m² and <60 ml/min/1.73 m². In certain embodiments, ertugliflozin or a co-crystal or a pharmaceutically acceptable salt thereof is administered as a pharmaceutical composition. In certain embodiments, the pharmaceutical composition comprises 5 mg or 15 mg of ertugliflozin or a co-crystal or a pharmaceutically acceptable salt thereof. In certain embodiments, ertugliflozin or a co-crystal or a pharmaceutically acceptable salt thereof is administered once daily.

In still other embodiments, the present invention is directed to a method of treating prediabetes, type 1 or type 2 diabetes mellitus comprising: a) determining that the eGFR of a patient in need of treatment for prediabetes, type 1 or type 2 diabetes is between ≥30 ml/min/1.73 m²; b) administering ertugliflozin or a co-crystal or a pharmaceutically acceptable salt thereof to the patient. In certain embodiments, the method comprises determining that the eGFR of a patient in need of treatment for prediabetes, type 1 or type 2 diabetes is between ≥30 ml/min/1.73 m² and <60 ml/min/1.73 m². In other embodiments, the method comprises a) determining that the eGFR of a patient in need of treatment for prediabetes, type 1 or type 2 diabetes is between ≥45 ml/min/1.73 m²; b) administering ertugliflozin or a co-crystal or a pharmaceutically acceptable salt thereof to the patient. In yet other embodiments, the method comprises determining that the eGFR of a patient in need of treatment for prediabetes, type 1 or type 2 diabetes is between ≥45 ml/min/1.73 m² and <60 ml/min/1.73 m². In certain embodiments, ertugliflozin or a co-crystal or a pharmaceutically acceptable salt thereof is administered as a pharmaceutical composition. In certain embodiments, the pharmaceutical composition comprises 5 mg or 15 mg of ertugliflozin or a co-crystal or a pharmaceutically acceptable salt thereof. In certain embodiments, ertugliflozin or a co-crystal or a pharmaceutically acceptable salt thereof is administered once daily.

Other embodiments described herein are directed to a method of lowering urinary albumin excretion in a patient, wherein the patient has moderate renal impairment or stage 3 chronic kidney disease (CKD). In certain embodiments, the patient has moderate renal impairment or stage 3A chronic kidney disease (CKD). In other embodiments, the patient has moderate B renal impairment or stage 3B chronic kidney disease (CKD). In certain embodiments, ertugliflozin or a co-crystal or a pharmaceutically acceptable salt thereof is administered as a pharmaceutical composition. In certain embodiments, the pharmaceutical composition comprises 5 mg or 15 mg of ertugliflozin or a co-crystal or a pharmaceutically acceptable salt thereof. In certain embodiments, ertugliflozin or a co-crystal or a pharmaceutically acceptable salt thereof is administered once daily.

In certain embodiments of the methods described herein, the method results in decreased blood pressure and decreased uric acid.

Another aspect of the present invention is a pharmaceutical composition to be used in the methods described that comprises (1) a compound of the present invention, and (2) a pharmaceutically acceptable excipient, diluent, or carrier. Preferably, the composition comprises a therapeutically effective amount of a compound of the present invention. The composition may also contain at least one additional pharmaceutical agent (described herein). Preferred agents include anti-obesity agents and/or anti-diabetic agents (described herein below).

Also, the methods described herein include compounds described herein administered in combination with other pharmaceutical agents (in particular, anti-obesity and anti-diabetic agents described herein below). The combination therapy may be administered as (a) a single pharmaceutical composition which comprises a compound of the present invention, at least one additional pharmaceutical agent described herein and a pharmaceutically acceptable excipient, diluent, or carrier; or (b) two separate pharmaceutical compositions comprising (i) a first composition comprising a compound of the present invention and a pharmaceutically acceptable excipient, diluent, or carrier, and (ii) a second composition comprising at least one additional pharmaceutical agent described herein and a pharmaceutically acceptable excipient, diluent, or carrier. The pharmaceutical compositions may be administered simultaneously or sequentially and in any order.

In certain embodiments, the methods described herein include administering 5 mg or 15 mg of ertugliflozin or a co-crystal or a pharmaceutically acceptable salt thereof in combination with 25 mg or 50 mg of sitagliptin or a pharmaceutically acceptable salt thereon. In other embodiments, the methods described herein include administering 5 mg or 15 mg of ertugliflozin or a co-crystal or a pharmaceutically acceptable salt thereof in combination with 1000 mg or 2000 mg of metformin. In still other embodiments, the methods described herein include administering 5 mg or 15 mg of ertugliflozin or a co-crystal or a pharmaceutically acceptable salt thereof in combination with 25 mg or 50 mg of sitagliptin or a pharmaceutically acceptable salt thereof and 1000 mg or 2000 mg of metformin.

It is to be understood that both the foregoing general description and the following detailed description are exemplary and explanatory only and are not restrictive of the invention, as claimed.

DETAILED DESCRIPTION

The present invention may be understood even more readily by reference to the following detailed description of exemplary embodiments of the invention and the examples included therein.

Before the present compounds, compositions and methods are disclosed and described, it is to be understood that this invention is not limited to specific synthetic methods of making that may of course vary. It is also to be understood that the terminology used herein is for the purpose of describing particular embodiments only and is not intended to be limiting. The plural and singular should be treated as interchangeable, other than the indication of number:

As used herein, the term "alkyl" refers to a hydrocarbon radical of the general formula $C_nH_{2n+1}$. The alkane radical may be straight or branched. For example, the term "($C_1$-$C_6$)alkyl" refers to a monovalent, straight, or branched aliphatic group containing 1 to 6 carbon atoms (e.g., methyl, ethyl, n-propyl, i-propyl, n-butyl, i-butyl, s-butyl, t-butyl, n-pentyl, 1-methylbutyl, 2-methylbutyl, 3-methylbutyl, neo-pentyl, 3,3-dimethylpropyl, hexyl, 2-methylpentyl, and the like). Similarly, the alkyl portion (i.e., alkyl moiety) of an alkoxy, acyl (e.g., alkanoyl), alkylamino, dialkylamino, alkylsulfonyl, and alkylthio group have the same definition as above. When indicated as being "optionally substituted", the alkane radical or alkyl moiety may be unsubstituted or substituted with one or more substituents (generally, one to three substituents except in the case of halogen substituents such as perchloro or perfluoroalkyls) independently selected from the group of substituents listed below in the definition for "substituted." "Halo-substituted alkyl" refers to an alkyl group substituted with one or more halogen atoms (e.g., fluoromethyl, difluoromethyl, trifluoromethyl, perfluoro-ethyl, 1,1-difluoroethyl and the like).

The term "cycloalkyl" refers to nonaromatic rings and may exist as a single ring, bicyclic ring or a spiro ring. Unless specified otherwise, the carbocyclic ring is generally a 3- to 8-membered ring. For example, cycloalkyl include groups such as cyclopropyl, cyclobutyl, cyclopentyl, cyclohexyl, cyclohexenyl, norbornyl (bicyclo[2.2.1]heptyl), bicyclo[2.2.2]octyl, and the like.

The term "heterocycle" refers to nonaromatic rings and may exist as a single ring, bicyclic ring or a spiral ring. Unless specified otherwise, the heterocyclic ring is generally a 3- to 6-membered ring containing 1 to 3 heteroatoms (preferably 1 or 2 heteroatoms) independently selected from sulfur, oxygen and/or nitrogen. Heterocyclic rings include groups such as epoxy, aziridinyl, tetrahydrofuranyl, pyrrolidinyl, N-methylpyrrolidinyl, piperidinyl, piperazinyl, pyrazolidinyl, 4H-pyranyl, morpholino, thiomorpholino, tetrahydrothienyl, tetrahydrothienyl 1,1-dioxide, and the like.

The phrase "therapeutically effective amount" means an amount of a compound of the present invention that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "animal" refers to humans (male or female), companion animals (e.g., dogs, cats and horses), food-source animals, zoo animals, marine animals, birds and other similar animal species.

The phrase "pharmaceutically acceptable" indicates that the substance or composition must be compatible chemically and/or toxicologically, with the other ingredients comprising a formulation, and/or the mammal being treated therewith.

The terms "treating", "treat", or "treatment" embrace both preventative, i.e., prophylactic, and palliative treatment.

The terms "modulated" or "modulating", or "modulate(s)", as used herein, unless otherwise indicated, refers to the inhibition of the sodium-glucose transporter (in particular, SGLT2) with compounds of the present invention thereby partially or fully preventing glucose transport across the transporter.

The term "preventing", as used herein, unless otherwise indicated, refers to reducing the likelihood or severity of neuronal damage following the incidence of ischemic stroke and close-head traumatic brain injury.

The term "compounds of the present invention" (unless specifically identified otherwise) refer to compounds of Formula (A), Formula (B) and all pure and mixed stereoisomers (including diastereoisomers and enantiomers), tautomers and isotopically labeled compounds. Hydrates and solvates of the compounds of the present invention are considered compositions of the present invention, wherein the compound is in association with water or solvent, respectively. The compounds may also exist in one or more crystalline states, i.e. as co-crystals, polymorphs, or they may exist as amorphous solids. All such forms are encompassed by the claims.

In one embodiment, $R^1$ is H, methyl, ethyl, propyl, isopropyl, methoxy, ethoxy, F, Cl, cyano, —$CF_3$, cyclopropyl, or cyclobutyl. In another embodiment, $R^1$ is H, methyl, ethyl, isopropyl, methoxy, ethoxy, F, Cl, cyano, —$CF_3$, or cyclopropyl. In a further embodiment, $R^1$ is H, methyl, ethyl, methoxy, ethoxy, F, Cl, cyano, —$CF_3$, or cyclopropyl. In yet a further embodiment, $R^1$ is methyl, ethyl, F, Cl, cyano, $CF_3$, or cyclopropyl.

In one embodiment, $R^2$ is methyl, ethyl, propyl, isopropyl, methoxy, ethoxy, F, Cl, cyano, —$CF_3$, —$CF_2CH_3$, ethynyl, 3-oxetanyloxy, 3-tetrahydrofuranyloxy, or cyclopropyl. In another embodiment, $R^2$ is methyl, ethyl, isopropyl, methoxy, ethoxy, F, Cl, cyano, —$CF_3$, —$CF_2CH_3$, ethynyl, 3-oxetanyloxy, 3-tetrahydrofuranyloxy, or cyclopropyl. In a further embodiment, $R^2$ is methyl, ethyl, methoxy, ethoxy, F, Cl, cyano, —$CF_3$, —$CF_2CH_3$, ethynyl, 3-oxetanyloxy, 3-tetrahydrofuranyloxy, or cyclopropyl. In yet a further embodiment, $R^2$ is methoxy or ethoxy.

"Ertugliflozin" means the compound of formula (4A):

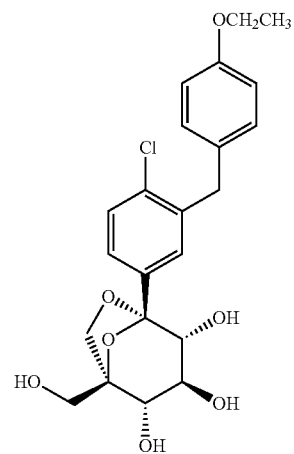

4A and has the chemical name having the chemical name (1S,2S,3S,4R,5S)-5-[4-chloro-3-(4-ethoxy-benzyl)-phenyl]-1-hydroxymethyl-6,8-dioxa-bicyclo[3.2.1]octane-2,3, 4-triol. In certain embodiments of the methods described herein ertugliflozin can exist as a co-crystal or a pharmaceutically acceptable salt.

In one embodiment, the crystal comprises the compound 4A and L-proline or L-pyroglutamic acid.

In a further embodiment, the crystal has one or more of the following:

a) space group of P2(1)2(1)2(1) and unit cell parameters substantially equal to the following:
a=7.4907(10) Å α=90°.
b=12.8626(15) Å β=90°.
c=28.029(4) Å γ=90°;

b) a powder x-ray diffraction pattern comprising 2-theta values of (CuKα radiation, wavelength of 1.54056 Å) 6.4±0.2, 16.7±0.2, 17.4±0.2 and 21.1±0.2;

c) a solid state 13C NMR spectrum having peak positions at 16.5±0.2, 131.1±0.2, 158.7±0.2, and 181.5±0.2 ppm as determined on a 500 MHz spectrometer relative to crystalline adamantine of 29.5 ppm; or d) a differential scanning calorimetry thermogram having an endotherm of about 142.5±2° C.

In a further embodiment, the crystal is a co-crystal comprising the compound of formula (4A) and L-pyroglutamic acid in a 1:1 stochiometric ratio.

The term "glomerular filtration rate (GFR)" refers to the volume of fluid filtered from the renal (kidney) glomerular capillaries into the Bowman's capsule per unit time. It is indicative of overall kidney function. The glomerular filtration rate (GFR) can be calculated by measuring any chemical that has a steady level in the blood, and is freely filtered but neither reabsorbed nor secreted by the kidneys. The rate therefore measured is the quantity of the substance in the urine that originated from a calculable volume of blood. The GFR is typically recorded in units of volume per time, e.g., milliliters per minute and the formula below can be used:

GFR=(Urine Concentration.times.Urine Volume)/Plasma Concentration

The GFR can be determined by injecting inulin into the plasma. Since inulin is neither reabsorbed nor secreted by the kidney after glomerular filtration, its rate of excretion is directly proportional to the rate of filtration of water and solutes across the glomerular filter. A normal value is: GFR=90-125 mL/min/1.73 m$^2$, in particular GFR=100-125 mL/min/1.73 m$^2$. Other principles to determine GFR involve measuring 51Cr-EDTA, iothalamate or iohexol.

The phrase "estimated glomerular filtration rate (eGFR)" is derived at screening from serum creatinine values based on e.g., the Chronic Kidney Disease Epidemiology Collaboration (CKD-EPI) equation, the Cockcroft-Gault formula or the Modification of Diet in Renal Disease (MDRD) formula, which are all known in the art.

Compounds used in the methods of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, New York. (1967-1999 ed.), or *Beilsteins Handbuch der organischen Chemie*, 4, Aufl. ed. Springer-Verlag, Berlin, including supplements (also available via the *Beilstein* online database)).

For illustrative purposes, the reaction schemes depicted below provide potential routes for synthesizing the compounds of the present invention as well as key intermediates. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the present invention, protection of remote functionality of intermediates may be necessary. The need for such protection will vary depending on the nature of the remote functionality and the conditions of the preparation methods. A "hydroxy-protecting group" refers to a substituent of a hydroxy group that blocks or protects the hydroxy functionality. Suitable hydroxyl-protecting groups (O-Pg) include for example, allyl, acetyl (Ac), silyl (like trimethylsily (TMS) or tert-butyldimethylsilyl (TBS)), benzyl (Bn), para-methoxybenzyl (PMB), trityl (Tr), para-bromobenzoyl, para-nitrobenzoyl and the like (benzylidene for protection of 1,3-diols). The need for such protection is readily determined by one skilled in the art. For a general description of protecting groups and their use, see T. W. Greene, *Protective Groups in Organic Synthesis*, John Wiley & Sons, New York, 1991.

Scheme 1 outlines the general procedures one could use to provide compounds of the present invention.

Scheme 1

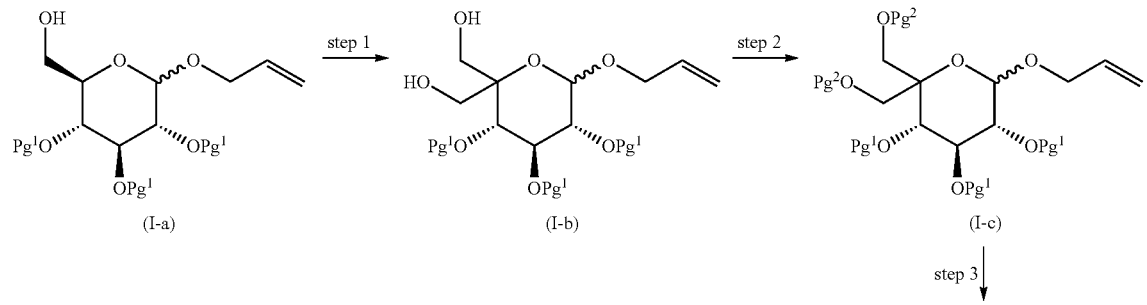

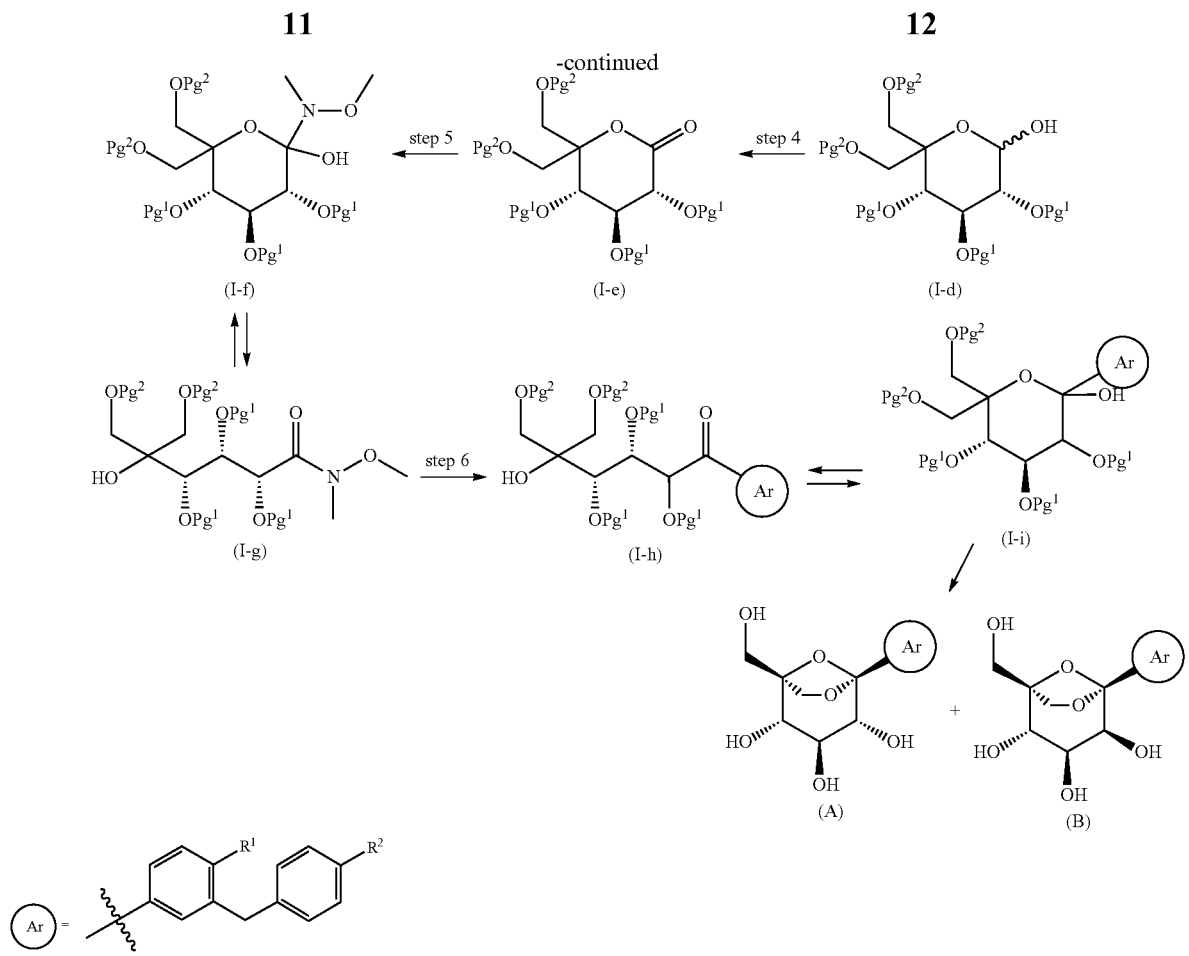

Allyl 2,3,4-tri-O-benzyl-D-glucopyranoside (I-a, where $Pg^1$ is a benzyl group) can be prepared by procedures described by Shinya Hanashima, et al., in *Bioorganic & Medicinal Chemistry*, 9, 367 (2001); Patricia A. Gent et al. in *Journal of the Chemical Society, Perkin* 1, 1835 (1974); Hans Peter Wessel in the *Journal of Carbohydrate Chemistry*, 7, 263, (1988); or Yoko Yuasa, et al., in *Organic Process Research & Development*, 8, 405-407 (2004). In step 1 of Scheme 1, the hydroxymethylene group can be introduced onto the glycoside by means of a Swern oxidation followed by treatment with formaldehyde in the presence of an alkali metal hydroxide (e.g., sodium hydroxide). This is referred to as an aldol-Cannizzaro reaction. The Swern oxidation is described by Kanji Omura and Daniel Swern in *Tetrahedron*, 34, 1651 (1978). Modifications of this process known to those of skill in the art may also be used. For example, other oxidants, like stabilized 2-iodoxybenzoic acid described by Ozanne, A. et al. in *Organic Letters*, 5, 2903 (2003), as well as other oxidants known by those skilled in the art can also be used. The aldol Cannizzaro sequence has been described by Robert Schaffer in the *Journal of The American Chemical Society*, 81, 5452 (1959) and Amigues, E. J., et al., in *Tetrahedron*, 63, 10042 (2007).

In step 2 of Scheme 1, protecting groups ($Pg^2$) can be added by treating intermediate (I-b) with the appropriate reagents and procedures for the particular protecting group desired. For example, p-methoxybenzyl (PMB) groups may be introduced by treatment of intermediate (I-b) with p-methoxybenzyl bromide or p-methoxybenzyl chloride in the presence of sodium hydride, potassium hydride, potassium tert-butoxide in a solvent like tetrahydrofuran, 1,2-dimethoxyethane or N,N-dimethylformamide (DMF). Conditions involving para-methoxybenzyltrichloroacetimidate in presence of a catalytic amount of acid (e.g., trifluoromethanesulfonic acid, methanesulfonic acid, or camphorsulfonic acid) in a solvent such as dichloromethane, heptane or hexanes can also be used. Benzyl (Bn) groups may be introduced by treatment of intermediate (I-b) with benzyl bromide or benzyl chloride in the presence of sodium hydride, potassium hydride, potassium tert-butoxide in a solvent like tetrahydrofuran, 1,2-dimethoxyethane or N,N-dimethylformamide. Conditions involving benzyltrichloroacetimidate in presence of a catalytic amount of acid (e.g., trifluoromethanesulfonic acid, methanesulfonic acid, or camphorsulfonic acid) in a solvent such as dichloromethane, heptane or hexanes can also be used.

In step 3 of Scheme 1, the allyl protection group is removed (e.g., by treatment with palladium chloride in methanol; cosolvent like dichloromethane may also be used; other conditions known by those skilled in the art could also be used, see T. W. Greene, *Protective Groups in Organic Synthesis*, John Wiley & Sons, New York, 1991) to form the lactol (I-d).

In step 4 of Scheme 1, oxidation of the unprotected hydroxyl group to an oxo group (e.g., Swern oxidation) then forms the lactone (I-e).

In step 5 of Scheme 1, the lactone (I-e) is reacted with N,O-dimethyl hydroxylamine hydrochloride to form the corresponding Weinreb amide which may exist in equilibrium in a closed/opened form. (I-f/I-g). The "Weinreb amide" (I-g) can be made using procedures well known to those of skill in the art. See, Nahm, S., and S. M. Weinreb, *Tetrahedron Letters*, 22 (39), 3815-1818 (1981). For example, intermediate (I-f/I-g) can be prepared from the commercially available N,O-dimethylhydroxylamine hydrochloride and an activating agent (e.g., trimethylaluminum).

In step 6 of Scheme 1, the aryl benzyl group (Ar) is introduced using the desired organometallic reagent (e.g., organo lithium compound (ArLi) or organomagnesium compound (ArMgX)) in tetrahydrofuran (THF) at a temperature ranging from about −78° C. to about 20° C. followed by hydrolysis (upon standing in protic conditions) to the corresponding lactol (I-i) which may be in equilibrium with the corresponding ketone (I-h). The bridged ketal motif found in (A) and (B) can be prepared by removing the protecting groups ($Pg^2$) using the appropriate reagents for the protecting groups employed. For example, the, p-methoxybenzyl (PMB) protecting groups may be removed by treatment with trifluoroacetic acid in the presence of anisole and dichloromethane (DCM) at about 0° C. to about 23° C. (room temperature). The remaining protecting groups ($Pg^1$) may then be removed using the appropriate chemistry for the particular protecting groups. For example, benzyl protecting groups may be removed by treating with formic acid in the presence of palladium (Pd black) in a protic solvent (e.g., ethanol/THF) at about room temperature to produce the final products (A) and (B). When $R^1$ is CN, the use of a Lewis acid like boron trichloride at a temperature ranging from about −78° C. to about room temperature in a solvent like dichloromethane or 1,2-dichloroethane may also be used to remove benzyl protective and/or para-methoxybenzyl protective groups.

When $R^1$ is CN and $R^2$ is ($C_1$-$C_4$)alkoxy in intermediate (I-i) or in products (A) or (B), upon treatment with a Lewis acid such as boron trichloride or boron tribomide, partial to complete de-alkylation to the corresponding phenol may occur to lead to the corresponding compound (A) or (B) where $R^1$ is CN and $R^2$ is OH. If this occurs, the ($C_1$-$C_4$) alkoxy group may be re-introduced via selective alkylation using a ($C_1$-$C_4$) alkyl iodide under mildly basic conditions, for example, potassium carbonate in acetone at a temperature ranging from about room temperature to about 56 degrees Celsius.

When $R^1$ and/or $R^2$ is ($C_1$-$C_4$)alkyl-$SO_2$— it is understood by one skilled in the art that the organometallic addition step 6 (Scheme 1) will be carried out on the corresponding ($C_1$-$C_4$)alkyl-S— containing organometallic reagent. The thio-alkyl is then oxidized at a later stage to the corresponding sulfone using conventional methods known by those skilled in the art.

The compounds of the present invention may be prepared as co-crystals using any suitable method. A representative scheme for preparing such co-crystals is described in Scheme 2.

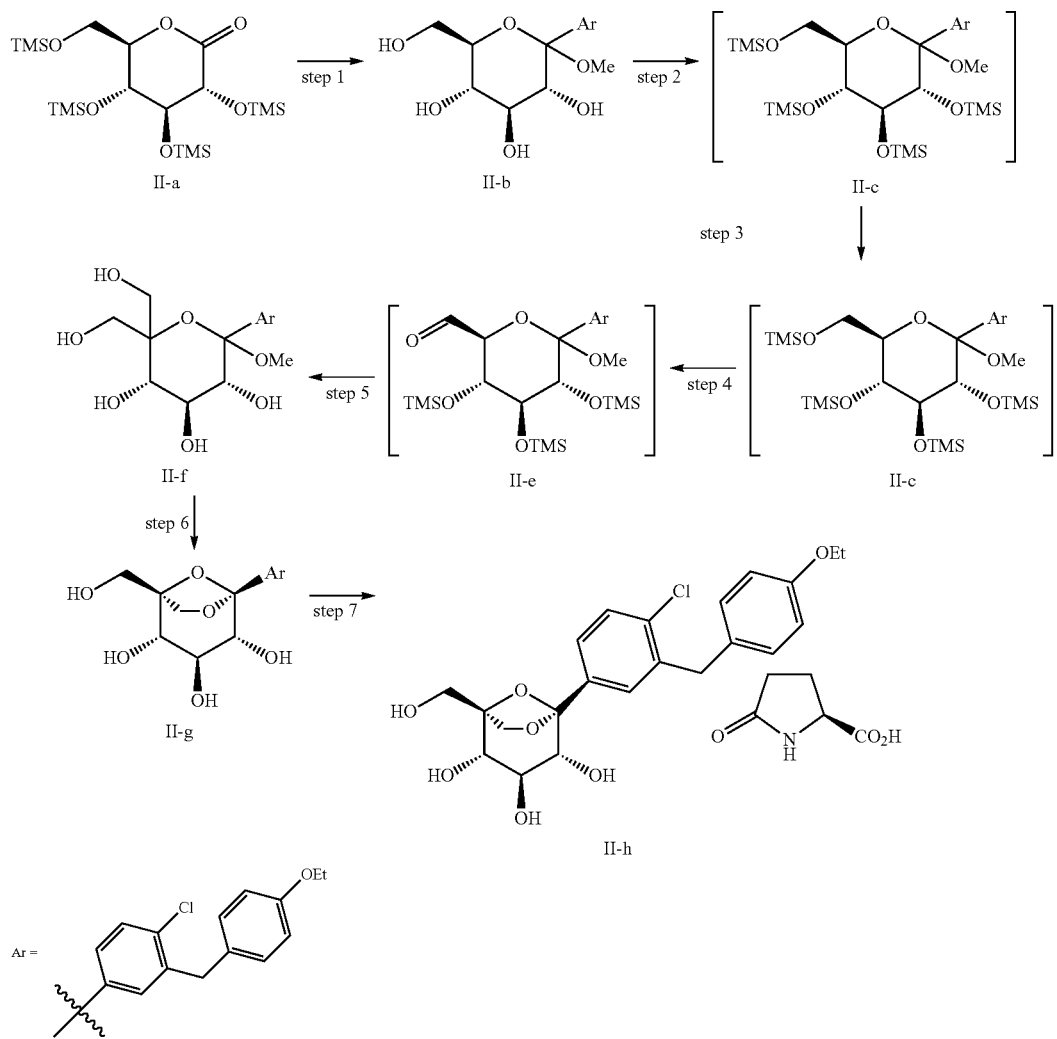

In Scheme 2, wherein Me is methyl and Et is ethyl, in step 1, 1-(5-bromo-2-chlorobenzyl)-4-ethoxybenzene is dissolved in 3:1, toluene: tetrahydrofuran followed by cooling the resulting solution to <−70° C. To this solution is added hexyllithium while maintaining the reaction at ≤−65° C. followed by stirring for 1 hour. (3R,4S,5R,6R)-3,4,5-tris(trimethylsilyloxy)-6-((trimethylsilyloxy)methyl)-tetrahydropyran-2-one (II-a) is dissolved in toluene and the resulting solution is cooled to −15° C. This solution is then added to the −70° C. aryllithium solution followed by stirring for 1 hour. A solution of methanesulfonic acid in methanol is then added followed by warming to room temperature and stirring for 16 to 24 hours. The reaction is deemed complete when the α-anomer level is ≤3%. The reaction is then basified by the addition of 5 M aqueous sodium hydroxide solution. The resulting salts are filtered off followed by concentration of the crude product solution. 2-methyltetrahydrofuran is added as a co-solvent and the organic phase is extracted twice with water. The organic phase is then concentrated to 4 volumes in toluene. This concentrate is then added to a 5:1, heptane: toluene solution causing precipitate to form. The solids are collected and dried under vacuum to afford a solid.

In step 2 of Scheme 2, to (II-b) in methylene chloride is added imidazole followed by cooling to 0° C. and then addition of trimethylsilylchloride to give the persilylated product. The reaction is warmed to room temperature and quenched by the addition of water, and the organic phase is washed with water. This crude methylene chloride solution of (II-c) is dried over sodium sulfate and then taken on crude into the next step.

In step 3 of Scheme 2, the crude solution of (II-c) in methylene chloride is concentrated to low volume and then the solvent is exchanged to methanol. The methanol solution of (II-c) is cooled to 0° C., then 1 mol % of potassium carbonate is added as a solution in methanol followed by stirring for 5 hours. The reaction is then quenched by addition of 1 mol % acetic acid in methanol, followed by warming to room temperature, solvent exchange to ethyl acetate, and then filtration of the minor amount of inorganic solids. The crude ethyl acetate solution of (II-d) is taken directly into the next step.

In step 4 of Scheme 2, the crude solution of (II-d) is concentrated to low volume, then diluted with methylene chloride and dimethylsulfoxide. Triethylamine is added followed by cooling to 10° C. and then sulfur trioxide pyridine complex is added in 3 portions as a solid at 10 minute intervals. The reaction is stirred an additional 3 hours at 10° C. before quenching with water and warming to room temperature. The phases are separated followed by washing the methylene chloride layer with aqueous ammonium chloride. The crude methylene chloride solution of (II-e) is taken directly into the next step.

In step 5 of Scheme 2, the crude solution of (II-e) is concentrated to low volume and then the solvent is exchanged to ethanol. Thirty equivalents of aqueous formaldehyde is added followed by warming to 55° C. An aqueous solution of 2 equivalents of potassium phosphate, tribasic is added followed by stirring for 24 hours at 55° C. The reaction temperature is then raised to 70° C. for an additional 12 hours. The reaction is cooled to room temperature, diluted with tert-butyl methyl ether and brine. The phases are separated followed by solvent exchange of the organic phase to ethyl acetate. The ethyl acetate phase is washed with brine and concentrated to low volume. The crude concentrate is then purified by silica gel flash chromatography eluting with 5% methanol, 95% toluene. Product containing fractions are combined and concentrated to low volume. Methanol is added followed by stirring until precipitation occurs. The suspension is cooled and the solids are collected and rinsed with heptane followed by drying. Product (II-f) is isolated as a solid.

In step 6 of Scheme 2, compound (II-f) is dissolved in 5 volumes of methylene chloride followed by the addition of 1 mol % SiliaBond® tosic acid and stirring for 18 hours at room temperature. The acid catalyst is filtered off and the methylene chloride solution of (II-g) is taken directly into the next step co-crystallization procedure.

In step 7 of Scheme 2, the methylene chloride solution of (II-g) is concentrated and then the solvent is exchanged to 2-propanol. Water is added followed by warming to 55° C. An aqueous solution of L-pyroglutamic acid is added followed by cooling the resulting solution to room temperature. The solution is then seeded and granulated for 18 hours. After cooling, the solids are collected and rinsed with heptane followed by drying. Product (II-h) is isolated as a solid.

An alternative synthesis route for compounds (A) of the present invention is depicted in Scheme 3 and described below.

Scheme 3

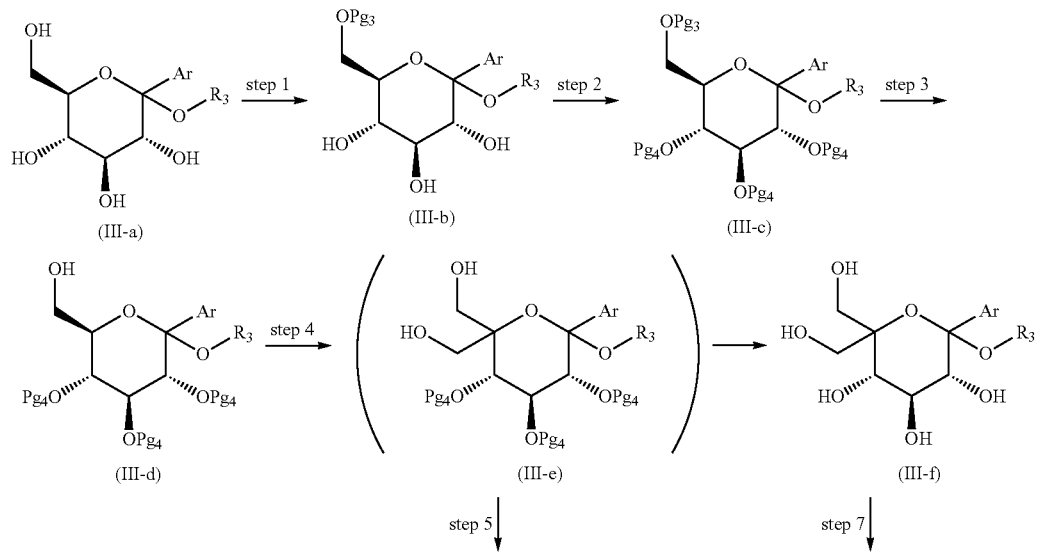

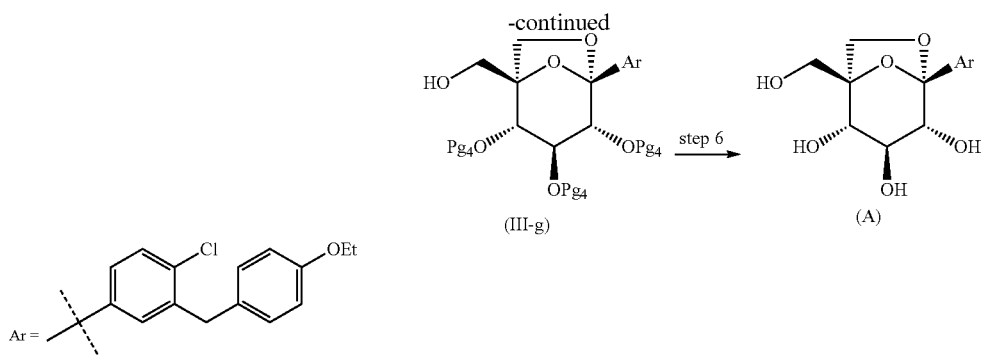

(III-g)　　　(A)

The synthesis of (III-a), where R₃ is an alkyl or fluoro substituted alkyl (except for the carbon adjacent to the oxygen atom) can be prepared in a similar way as described in step 1 of Scheme 2. In step 1 of Scheme 3, the primary hydroxyl group is selectively protected by an appropriate protective group. For example, a trityl group (Pg₃=Tr) can be introduced by treatment of intermediate (III-a) with chlorotriphenylmethane in presence of a base like pyridine in a solvent like toluene, tetrahydrofuran or dichloromethane at a temperature ranging from about 0 degrees Celsius to about room temperature. Additional examples of such protective groups and experimental conditions are known by those skilled in the art and can be found in T. W. Greene, *Protective Groups in Organic Synthesis*, John Wiley & Sons, New York, 1991.

In step 2 of Scheme 3, the secondary hydroxyl groups can be protected by the appropriate protecting groups. For example, benzyl groups (Pg₄ is Bn) can be introduced by treatment of intermediate (III-b) with benzyl bromide or benzyl chloride in the presence of sodium hydride, potassium hydride, potassium tert-butoxide in a solvent like tetrahydrofuran, 1,2-dimethoxyethane or N,N-dimethylformamide at a temperature ranging from about 0 degrees Celsius to about 80 degrees Celsius. Acetyl or benzoyl groups (Pg₄=Ac or Bz) may be introduced by treatment of intermediate (III-b) with acetyl chloride, acetyl bromide or acetic anhydride or benzoyl chloride or benzoic anhydride in the presence of a base like triethylamine, N,N-diisopropylethylamine or 4-(dimethylamino)pyridine in a solvent like tetrahydrofuran, 1,2-dimethoxyethane or dichloromethane at a temperature ranging from about 0 degrees Celsius to about 80 degrees Celsius.

In step 3 of Scheme 3, the primary hydroxyl group is deprotected to lead to intermediate (III-d). When Pg₃ is Tr, intermediate (III-c) is treated in the presence of an acid like para-toluenesulfonic acid in an alcoholic solvent like methanol at a temperature ranging from about −20 degrees Celsius to about room temperature to provide intermediate (III-d). Cosolvents like chloroform may be used.

In step 4 of Scheme 3, a hydroxymethylene group is introduced through a process similar to the one already described in Scheme 1 (step 1) and Scheme 2 (steps 4 and 5). Other sources of formaldehyde, like paraformaldehyde in a solvent like ethanol at a temperature ranging from about room temperature to about 70 degrees Celsius in the presence of an alkali metal alkoxide can also be used in this step. When Pg₄ is Bn, this step provides intermediate (III-e) and when Pg₄ is Ac or Bz, this step provides intermediate (III-f).

In step 5 of Scheme 3, intermediate (III-e) is treated with an acid like trifluoroacetic acid or an acidic resin in a solvent like dichloromethane at a temperature ranging from about −10 degrees Celsius to about room temperature to produce intermediate (III-g).

In step 6 of Scheme 3, the remaining protecting groups (Pg₄) may then be removed using the appropriate chemistry for the particular protecting groups. For example, benzyl protecting groups may be removed by treating with formic acid in the presence of palladium (Pd black) in a protic solvent (e.g., ethanol/THF) at about room temperature to produce the final product (A).

In step 7 of Scheme 3, intermediate (III-f) is treated with an acid like trifluoroacetic acid or an acidic resin in a solvent like dichloromethane at a temperature ranging from about −10 degrees Celsius to about room temperature to produce the final product (A).

Another alternative scheme for synthesizing product (A) is depicted in Scheme 4 and described below.

Scheme 4

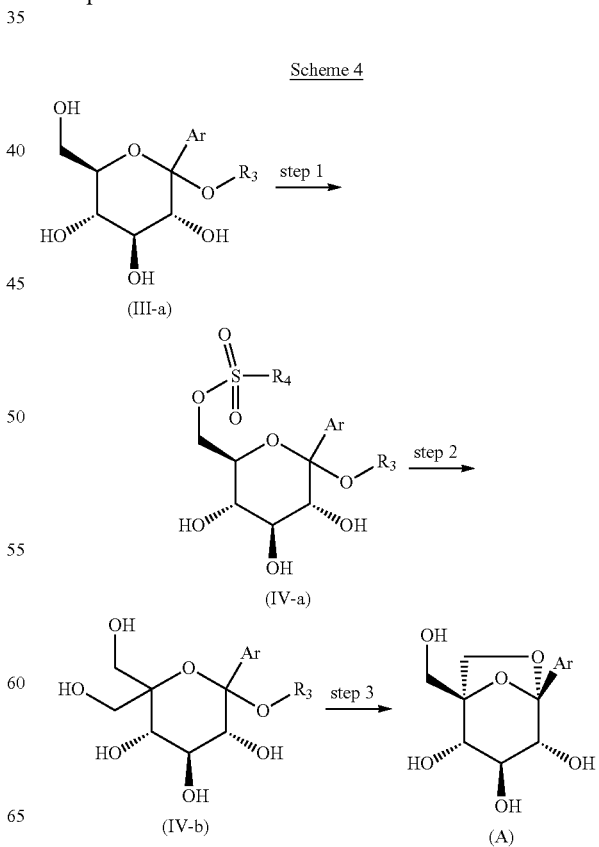

19

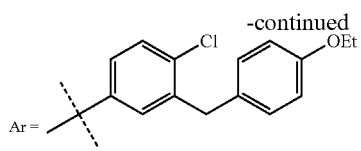

-continued

In step 1 of Scheme 4, intermediate (III-a) is treated with the appropriate arylsulfonyl chloride $R_4SO_2Cl$ or arylsulfonic anhydride $R_4S(O)_2OS(O)_2R_4$ (wherein $R_4$ is an optionally substituted aryl group, such as found in the arylsulfonyl chlorides 4-methyl-benzenesulfonyl chloride, 4-nitro-benzenesulfonyl chloride, 4-fluoro-benzenesulfonyl chloride, 2,6-dichloro-benzenesulfonyl chloride, 4-fluoro-2-methyl-benzenesulfonyl chloride, and 2,4,6-trichloro-benzenesulfonyl chloride, and in the arylsulfonic anhydride, p-toluenesulfonic anhydride) in presence of a base like pyridine, triethylamine, N,N-diisopropylethylamine in a solvent like tetrahydrofuran, 2-methyltetrahydrofuran at a temperature ranging from about −20 degrees Celsius to about room temperature. Some Lewis acids like zinc(II) bromide may be used as additives.

20

In step 2 of Scheme 4, intermediate (IV-a) is submitted to a Kornblum-type oxidation (see, Kornblum, N., et al., *Journal of The American Chemical Society*, 81, 4113 (1959)) to produce the corresponding aldehyde which may exist in equilibrium with the corresponding hydrate and/or hemiacetal form. For example intermediate (IV-a) is treated in the presence of a base like pyridine, 2,6-lutidine, 2,4,6-collidine, N,N-diisopropylethylamine, 4-(dimethylamino) pyridine in a solvent like dimethyl sulfoxide at a temperature ranging from about room temperature to about 150 degrees Celsius. The aldehyde intermediate produced is then submitted to the aldol/Cannizzaro conditions described for step 1 (Scheme 1) and step 5 (Scheme 2) to produce intermediate (IV-b).

In step 3 of Scheme 4, intermediate (IV-b) is treated with an acid like trifluoroacetic acid or an acidic resin in a solvent like dichloromethane at a temperature ranging from about −10 degrees Celsius to about room temperature to produce the final product (A).

When $R^2$ is $(C_2-C_4)$alkynyl the process may be performed using Scheme 5, wherein $R^6$ is H or $(C_1-C_2)$alkyl.

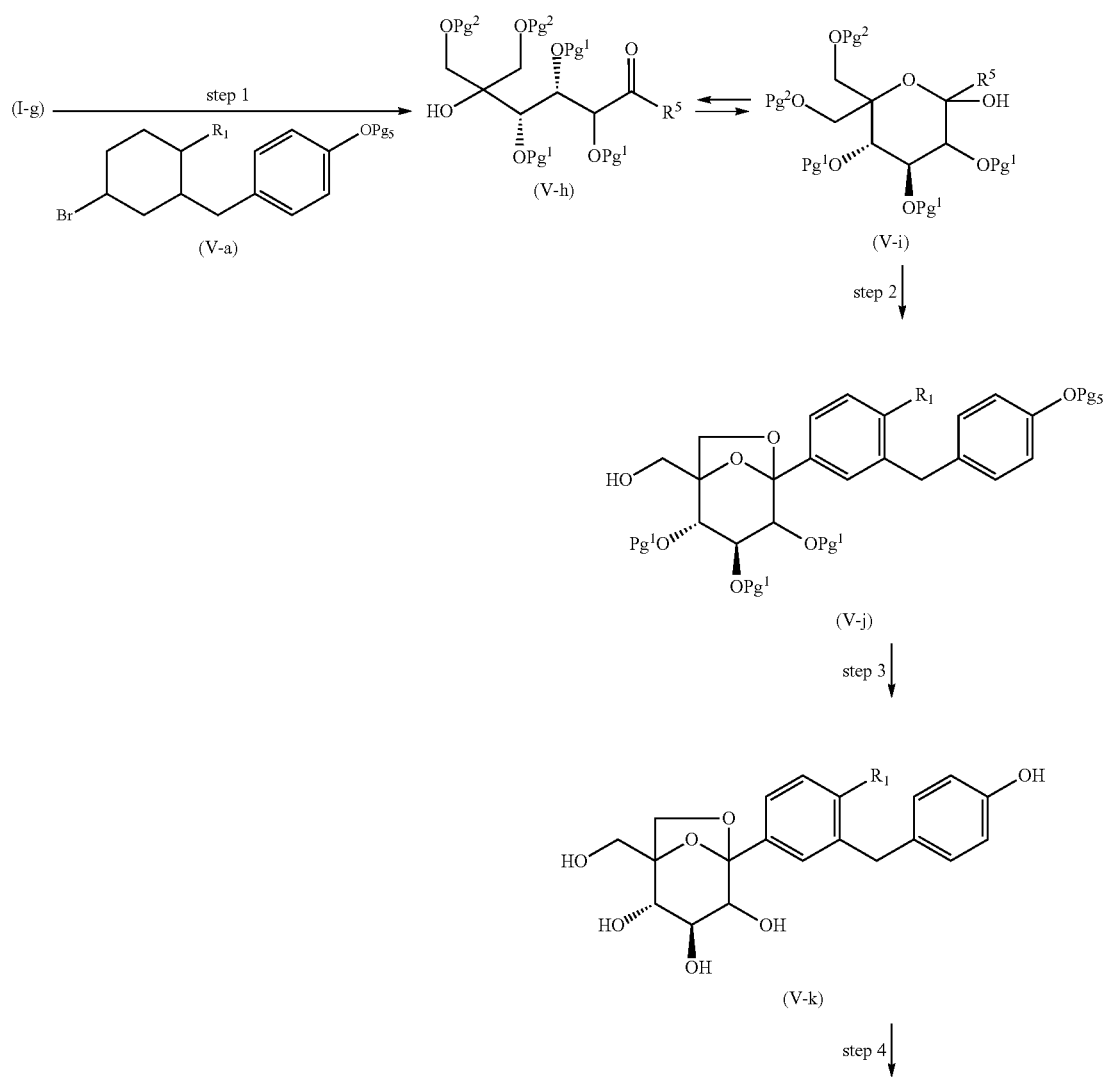

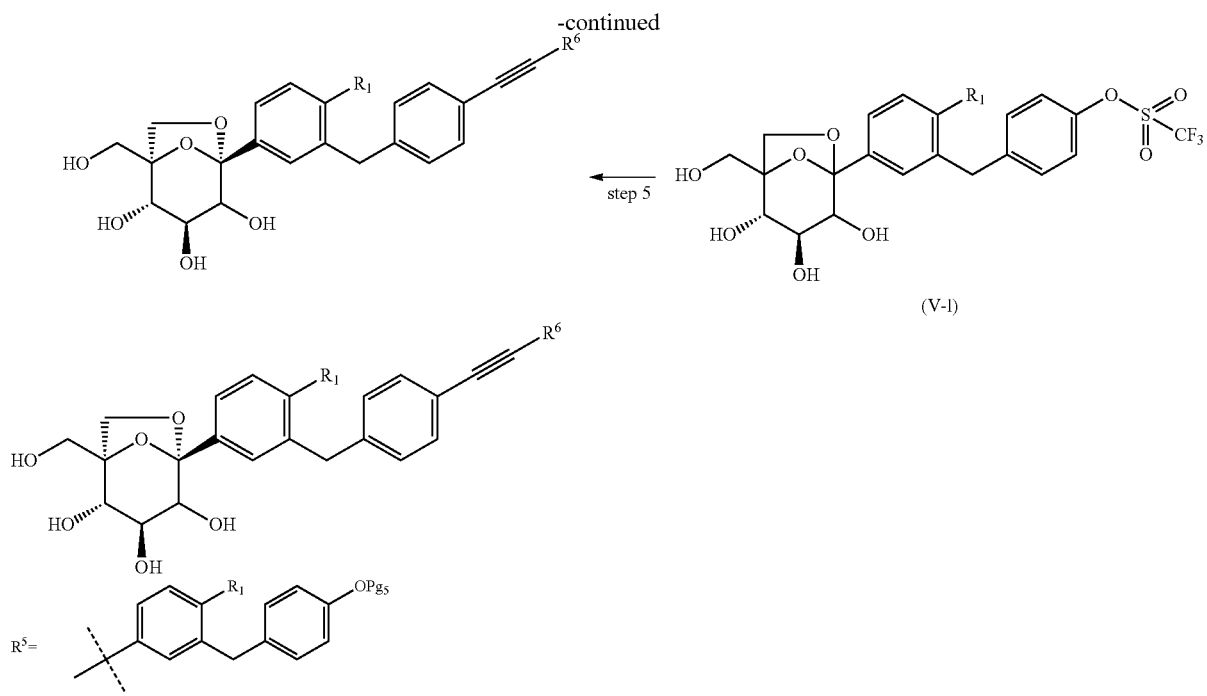

In step 1 of Scheme 5, which provides intermediate (V-i), the organometallic addition step is carried out in a similar way to the one described in Scheme 1, step 6, using the organometallic reagent derived from (V-a), where $Pg_5$ is a suitable protective group for the hydroxyl group. For instance $Pg_5$ can be a tert-butyldimethylsilyl group (TBS) (see US2007/0054867 for preparation of for instance {4-[(5-bromo-2-chloro-phenyl)-methyl]-phenoxy}-tert-butyl-dimethyl-silane).

In step 2 of Scheme 5, when $Pg^2$=PMB, intermediate (V-i) is treated with an acid like trifluoroacetic acid, methanesulfonic acid or an acidic resin in presence of anisole in a solvent like dichloromethane at a temperature ranging from about −10 degrees Celsius to about room temperature to produce intermediate (V-j).

In step 3 of Scheme 5, protecting groups ($Pg_5$) and ($Pg^1$) can be removed to provide (V-k). Typically ($Pg_5$) is TBS and $Pg^1$ is Bn. In this circumstance, the protecting groups are removed by sequential treatment of (V-j) with 1) tetrabutylammonium fluoride in a solvent like tetrahydrofuran or 2-methyltetrahydrofuran at a temperature ranging from 0 degrees Celsius to about 40 degrees Celsius and 2) treatment with formic acid in the presence of palladium (Pd black) in a protic solvent (e.g., ethanol/THF) at about room temperature. In this sequence, the order of the 2 reactions is interchangeable.

In step 4 of Scheme 5, intermediate (V-k) is treated with N,N-bis-(trifluoromethanesulfonyl)-aniline in presence of a base like triethylamine or 4-dimethylaminopyridine in a solvent like dichloromethane or 1,2-dichloroethane at a temperature ranging from 0 degrees Celsius to about 40 degrees Celsius to produce intermediate (V-l).

In step 5 of Scheme 5, intermediate (V-l) is subjected to a Sonogashira-type reaction (see, Sonogashira, K. Coupling Reactions Between sp$^2$ and sp Carbon Centers. In *Comprehensive Organic Synthesis* (eds. Trost, B. M., Fleming, I.), 3, 521-549, (Pergamon, Oxford, 1991)). For instance (V-l) is treated with the appropriate terminal alkyne HCCR$^6$ in presence of copper(I) iodide, a catalyst like bis-(triphenylphosphine)-palladium dichloride or tetrakis(triphenylphosphine)palladium(0) in presence of a base like triethylamine or N,N-diisopropylethylamine in a solvent like N,N-dimethylformamide at a temperature ranging from about room temperature to about 120 degrees Celsius to produce the desired product (A) and (B). When R$^6$ is H, it is more convenient to use trimethylsilylacetylene. In this case the crude material obtained from the reaction described above is treated with a base like potassium carbonate in an alcoholic solvent like MeOH at about room temperature to produce after classical work-up known by those skilled in the art the desired product (A) and (B) where R$^2$ is —CCH.

One skilled in the art would understand that the chemistry described above in schemes 1 to 5, represents different ways of accessing intermediate (V-k). In turn, particularly when R$^1$ is Cl, (V-k) can be treated with an alkylating agent of choice under classical conditions to selectively alkylate the phenol group to produce (A) (and (B) in schemes 1 and 5) where R$^2$ is ($C_1$-$C_4$)alkoxy.

The compounds of the present invention contain asymmetric or chiral centers, and, therefore, exist in different stereoisomeric forms. Unless specified otherwise, it is intended that all stereoisomeric forms of the compounds of the present invention as well as mixtures thereof, including racemic mixtures, form part of the present invention. In addition, the present invention embraces all geometric and positional isomers. For example, if a compound of the present invention incorporates a double bond or a fused ring, both the cis- and trans-forms, as well as mixtures, are embraced within the scope of the invention.

Diastereomeric mixtures can be separated into their individual diastereoisomers on the basis of their physical chemical differences by methods well known to those skilled in the art, such as by chromatography and/or fractional crystallization, distillation, sublimation. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC (high pressure liquid chromatography) column.

It is also possible that the intermediates and compounds of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. A specific example of a proton tautomer is the imidazole moiety where the proton may migrate between the two ring nitrogens. Valence tautomers include interconversions by reorganization of some of the bonding electrons. The equilibrium between closed and opened form of some intermediates (and/or mixtures of intermediates) is reminiscent of the process of mutarotation involving aldoses, known by those skilled in the art.

The present invention also embraces isotopically-labeled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine, iodine, and chlorine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{123}$I, $^{125}$I and $^{36}$Cl, respectively.

Certain isotopically-labeled compounds of the present invention (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements), and hence may be preferred in some circumstances. Positron emitting isotopes such as $^{15}$O, $^{13}$N, $^{11}$C, and $^{18}$F are useful for positron emission tomography (PET) studies to examine substrate occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

The compounds described herein are used in the methods of the present invention for treating diseases, conditions and/or disorders modulated by the inhibition of the sodium-glucose transporters (in particular SGLT2) in patients with renal impairment or chronic kidney disease (CDK).

The present invention provides a method of treating diseases, conditions and/or disorders modulated by the inhibition of sodium-glucose transporters in an animal with renal impairment or chronic kidney disease (CDK) that includes administering to an animal in need of such treatment a therapeutically effective amount of a compound described herein or a pharmaceutical composition comprising an effective amount of a compound described herein and a pharmaceutically acceptable excipient, diluent, or carrier. The method is particularly useful for treating diseases, conditions and/or disorders that benefit from the inhibition of SGLT2.

In certain embodiments, the patients which may be amenable to the therapies of this invention may have or are at-risk for one or more of the following diseases, disorders or conditions: type 1 diabetes, type 2 diabetes, impaired glucose tolerance (IGT), impaired fasting blood glucose (IFG), hyperglycemia, postprandial hyperglycemia, postabsorptive hyperglycemia, latent autoimmune diabetes in adults (LADA), overweight, obesity, dyslipidemia, hyperlipidemia, hypercholesterolemia, hypertriglyceridemia, hyperNEFA-emia, postprandial lipemia, hypertension, atherosclerosis, endothelial dysfunction, osteoporosis, chronic systemic inflammation, nonalcoholic fatty liver disease (NAFLD), polycystic ovarian syndrome, metabolic syndrome, nephropathy, micro- or macroalbuminuria, proteinuria, retinopathy, cataracts, neuropathy, learning or memory impairment, neurodegenerative or cognitive disorders, cardiovascular diseases, tissue ischaemia, diabetic foot or ulcus, atherosclerosis, hypertension, endothelial dysfunction, myocardial infarction, acute coronary syndrome, unstable angina pectoris, stable angina pectoris, peripheral arterial occlusive disease, cardiomyopathy (including e.g. uremic cardiomyopathy), heart failure, cardiac hypertrophy, heart rhythm disorders, vascular restenosis, stroke, (renal, cardiac, cerebral or hepatic) ischemia/reperfusion injuries, (renal, cardiac, cerebral or hepatic) fibrosis, (renal, cardiac, cerebral or hepatic) vascular remodeling; a diabetic disease, especially type 2 diabetes, mellitus may be preferred (e.g. as underlying disease).

In one embodiment, the present invention provides a method for using ertugliflozin in one or more of the following methods: preventing, slowing the progression of, delaying or treating a metabolic disorder selected from the group consisting of type 2 diabetes mellitus, impaired glucose tolerance, impaired fasting blood glucose, hyperglycemia, postprandial hyperglycemia, hyperinsulinemia and metabolic syndrome; or slowing the progression of, delaying or treating of pre-diabetes; or preventing, slowing the progression of, delaying or treating of an onset of type 2 diabetes mellitus; or improving glycemic control and/or for reducing of fasting plasma glucose, of postprandial plasma glucose and/or of glycosylated hemoglobin HbA1c; or preventing, slowing, delaying or reversing progression from impaired glucose tolerance, impaired fasting blood glucose, insulin resistance or from metabolic syndrome to type 2 diabetes mellitus; or preventing, slowing the progression of, delaying or treating of a condition or disorder selected from the group consisting of complications of diabetes mellitus such as cataracts and micro- and macrovascular diseases, such as nephropathy, retinopathy, neuropathy, tissue ischaemia, diabetic foot, dyslipidemia, arteriosclerosis, myocardial infarction, acute coronary syndrome, unstable angina pectoris, stable angina pectoris, stroke, peripheral arterial occlusive disease, cardiomyopathy, heart failure, heart rhythm disorders and vascular restenosis; or reducing body weight and/or body fat, or preventing an increase in body weight and/or body fat, or facilitating a reduction in body weight and/or body fat; or preventing, slowing, delaying or treating the degeneration of pancreatic beta cells and/or the decline of the functionality of pancreatic beta cells and/or for improving and/or restoring the functionality of pancreatic beta cells and/or restoring the functionality of pancreatic insulin secretion; or preventing, slowing, delaying or treating diseases or conditions attributed to an abnormal accumulation of ectopic fat, in particular liver fat; or for maintaining and/or improving the insulin sensitivity and/or for treating or preventing hyperinsulinemia and/or insulin resistance; in a patient with renal impairment or chronic kidney disease (CDK), in particular a patient with mild or moderate renal impairment.

In one embodiment, the method comprises treating prediabetes, type 1 or type 2 diabetes mellitus. In one embodiment, the method comprises improving glycemic control in a patient with prediabetes, type 1 or type 2 diabetes mellitus.

In one embodiment, the present invention provides a method of treating prediabetes, type 1 or type 2 diabetes mellitus in patient comprising administering ertugliflozin or a co-crystal or a pharmaceutically acceptable salt thereof to the patient, wherein the patient has moderate renal impairment. In one embodiment, the patient has moderate A renal impairment. In one embodiment, the patient has moderate B renal impairment.

In one embodiment, the present invention further provides a method for improving glycemic control in a patient with prediabetes, type 1 or type 2 diabetes mellitus comprising administering ertugliflozin or a co-crystal or a pharmaceutically acceptable salt thereof to the patient, wherein the patient has moderate renal impairment. In one embodiment, the patient has moderate A renal impairment. In one embodiment, the patient has moderate B renal impairment.

In one embodiment, the present invention further provides a method of treating prediabetes, type 1 or type 2 diabetes mellitus in patient comprising administering ertugliflozin or a co-crystal or a pharmaceutically acceptable salt thereof to the patient, wherein the patient has stage 3 chronic kidney disease (CKD). In one embodiment, the patient has stage 3A chronic kidney disease (CKD). In one embodiment, the patient has stage 3B chronic kidney disease (CKD).

In one embodiment, the present invention further provides a method for improving glycemic control in a patient with prediabetes, type 1 or type 2 diabetes mellitus comprising administering ertugliflozin or a co-crystal or a pharmaceutically acceptable salt thereof to the patient, wherein the patient has stage 3 chronic kidney disease (CKD). In one embodiment, the patient has stage 3A chronic kidney disease (CKD). In one embodiment, the patient has stage 3B chronic kidney disease (CKD).

In one embodiment, the present invention further provides a method of treating prediabetes, type 1 or type 2 diabetes mellitus or improving glycemic control in a patient with prediabetes, type 1 or type 2 diabetes mellitus, said method comprising: a) assessing the renal function of a patient; b) treating a patient having moderate renal impairment with ertugliflozin or a co-crystal or a pharmaceutically acceptable salt thereof, but not treating a patient having severe renal impairment or kidney failure with ertugliflozin or a co-crystal or a pharmaceutically acceptable salt thereof.

In one embodiment, the method further comprises treating a patient having mild renal impairment or normal renal function with ertugliflozin or a co-crystal or a pharmaceutically acceptable salt thereof.

In one embodiment, the present invention further provides a method comprising: a) identifying a patient in need of treatment for type 2 diabetes mellitus; b) assessing the renal function of said patient; c) treating a patient having moderate renal impairment with ertugliflozin or a co-crystal or a pharmaceutically acceptable salt thereof, but not treating a patient having severe renal impairment or kidney failure with ertugliflozin or a co-crystal or a pharmaceutically acceptable salt thereof.

In one embodiment, the method further comprises treating a patient having mild renal impairment or normal renal function with ertugliflozin or a co-crystal or a pharmaceutically acceptable salt thereof.

In one embodiment, the present invention further provides a method of treating prediabetes, type 1 or type 2 diabetes mellitus or improving glycemic control in a patient with prediabetes, type 1 or type 2 diabetes mellitus, said method comprising: a) assessing the renal function of said patient; b) treating a patient having moderate A renal impairment with ertugliflozin or a co-crystal or a pharmaceutically acceptable salt thereof, but not treating a patient having moderate B renal impairment, severe renal impairment or kidney failure with ertugliflozin or a co-crystal or a pharmaceutically acceptable salt thereof.

In one embodiment, the method further comprises treating a patient having mild renal impairment or normal renal function with ertugliflozin or a co-crystal or a pharmaceutically acceptable salt thereof.

In one embodiment, the present invention further provides a method comprising: a) identifying a patient in need of treatment for type 2 diabetes mellitus; b) assessing the renal function of said patient; c) treating a patient having moderate A renal impairment with ertugliflozin or a co-crystal or a pharmaceutically acceptable salt thereof, but not treating a patient having moderate B renal impairment, severe renal impairment or kidney failure with ertugliflozin or a co-crystal or a pharmaceutically acceptable salt thereof.

In one embodiment, the method further comprises treating a patient having mild renal impairment or normal renal function with ertugliflozin or a co-crystal or a pharmaceutically acceptable salt thereof.

In one embodiment, the present invention further provides a method of treating type 2 diabetes comprising: a) determining the eGFR of a patient in need of treatment for prediabetes, type 1 or type 2 diabetes mellitus; b) administering ertugliflozin or a co-crystal or a pharmaceutically acceptable salt thereof to the patient, if the eGFR of the patient is ≥30 ml/min/1.73 m$^2$.

In one embodiment, ertugliflozin or a co-crystal or a pharmaceutically acceptable salt thereof is administered if the eGFR of the patient is between ≥30 ml/min/1.73 m$^2$ and <60 ml/min/1.73 m$^2$. In one embodiment, the method further comprises discontinuing ertugliflozin or a co-crystal or a pharmaceutically acceptable salt thereof if the eGFR of the patient falls below 30 ml/min/1.73 m$^2$. In one embodiment, ertugliflozin or a co-crystal or a pharmaceutically acceptable salt thereof is administered if the eGFR of the patient is between ≥45 ml/min/1.73 m$^2$ and <60 ml/min/1.73 m$^2$. In one embodiment, the method further comprises discontinuing ertugliflozin or a co-crystal or a pharmaceutically acceptable salt thereof if the eGFR of the patient falls below 45 ml/min/1.73 m$^2$.

In one embodiment, the present invention further provides a method comprising: a) assessing the renal function of a patient; b) administering ertugliflozin or a co-crystal or a pharmaceutically acceptable salt thereof to the patient; c) discontinuing ertugliflozin or a co-crystal or a pharmaceutically acceptable salt thereof if the eGFR of the patient falls below 30 ml/min/1.73 m$^2$.

In one embodiment, ertugliflozin or a co-crystal or a pharmaceutically acceptable salt thereof is administered if the eGFR of the patient is between ≥30 ml/min/1.73 m$^2$ and <60 ml/min/1.73 m$^2$.

In one embodiment, the present invention further provides a method comprising: a) assessing the renal function of a patient; b) administering ertugliflozin or a co-crystal or a pharmaceutically acceptable salt thereof to the patient; c)

discontinuing ertugliflozin or a co-crystal or a pharmaceutically acceptable salt thereof if the eGFR of the patient falls below 45 ml/min/1.73 m$^2$.

In one embodiment, ertugliflozin or a co-crystal or a pharmaceutically acceptable salt thereof is administered if the eGFR of the patient is between ≥45 ml/min/1.73 m$^2$ and <60 ml/min/1.73 m$^2$.

In one embodiment, the present invention further provides a method of treating prediabetes, type 1 or type 2 diabetes mellitus comprising: a) determining that the eGFR of a patient in need of treatment for type 2 diabetes mellitus is between 30 ml/min/1.73 m$^2$ and <60 ml/min/1.73 m$^2$; b) administering ertugliflozin or a co-crystal or a pharmaceutically acceptable salt thereof to the patient.

In one embodiment, the method further comprises discontinuing ertugliflozin or a co-crystal or a pharmaceutically acceptable salt thereof if the eGFR of the patient falls below 30 ml/min/1.73 m$^2$.

In one embodiment, the present invention further provides a method of treating prediabetes, type 1 or type 2 diabetes mellitus comprising: a) determining that the eGFR of a patient in need of treatment for type 2 diabetes mellitus is between ≥45 ml/min/1.73 m$^2$ and <60 ml/min/1.73 m$^2$; b) administering ertugliflozin or a co-crystal or a pharmaceutically acceptable salt thereof to the patient.

In one embodiment, the method further comprises discontinuing ertugliflozin or a co-crystal or a pharmaceutically acceptable salt thereof if the eGFR of the patient falls below 45 ml/min/1.73 m$^2$.

In one embodiment, the present invention further provides a method of treating prediabetes, type 1 or type 2 diabetes mellitus in a patient having an eGFR between 30 ml/min/1.73 m$^2$ and <60 ml/min/1.73 m$^2$ comprising: a) measuring the patient's eGFR b) measuring the effectiveness of ertugliflozin or a co-crystal or a pharmaceutically acceptable salt thereof for treatment of prediabetes, type 1 or type 2 diabetes mellitus in said patients; and c) administering ertugliflozin or a co-crystal or a pharmaceutically acceptable salt thereof to the patient.

In one embodiment, the patient has an eGFR between ≥45 ml/min/1.73 m$^2$ and <60 ml/min/1.73 m$^2$. The effectiveness of ertugliflozin is for example measured by determining the % HbA1c of the free plasma glucose (FPG) in the patient.

In one embodiment, the present invention further provides a method of treatment comprising: a) identifying a patient as being in need of treatment for prediabetes, type 1 or type 2 diabetes mellitus; b) determining that the patient's eGFR is ≥30 ml/min/1.73 m$^2$; c) selecting a prediabetes, type 1 or type 2 diabetes mellitus treatment for the patient that comprises the administration of ertugliflozin or a co-crystal or a pharmaceutically acceptable salt thereof, based on the recognition that ertugliflozin is effective for treatment of type 2 diabetes mellitus in patients whose eGFR is ≥30 ml/min/1.73 m$^2$ and not in patients whose eGFR is <30 ml/min/1.73 m$^2$; and d) administering ertugliflozin or a co-crystal or a pharmaceutically acceptable salt thereof to the patient.

In one embodiment, step b) comprises determining that the patient's eGFR is ≥30 ml/min/1.73 m$^2$ and <90 ml/min/1.73 m$^2$. In one embodiment, step b) comprises determining that the patient's eGFR is ≥30 ml/min/1.73 m$^2$ and <60 ml/min/1.73 m$^2$.

In one embodiment, the present invention further provides a method of treatment comprising: a) identifying a patient with prediabetes, type 1 or type 2 diabetes mellitus in need of improvement of glycemic control; b) determining that the patient's eGFR is ≥30 ml/min/1.73 m$^2$; c) selecting a prediabetes, type 1 or type 2 diabetes mellitus treatment for the patient that comprises the administration of ertugliflozin or a co-crystal or a pharmaceutically acceptable salt thereof, based on the recognition that ertugliflozin is effective for treatment of prediabetes, type 1 or type 2 diabetes mellitus in patients whose eGFR is ≥30 ml/min/1.73 m$^2$ and not in patients whose eGFR is <30 ml/min/1.73 m$^2$; and d) administering ertugliflozin or a co-crystal or a pharmaceutically acceptable salt thereof to the patient.

In one embodiment, step b) comprises determining that the patient's estimated glomerular filtration rate (eGFR) is ≥30 ml/min/1.73 m$^2$ and <90 ml/min/1.73 m$^2$. In one embodiment, step b) comprises determining that the patient's eGFR is ≥30 ml/min/1.73 m$^2$ and <60 ml/min/1.73 m$^2$.

In one embodiment, the present invention further provides a method of treatment comprising: a) identifying a patient as being in need of treatment for prediabetes, type 1 or type 2 diabetes mellitus; b) measuring the patient's eGFR; c) determining that the patient's eGFR is ≥30 ml/min/1.73 m$^2$ and <60 ml/min/1.73 m$^2$ d) prescribing a prediabetes, type 1 or type 2 diabetes mellitus treatment for the patient that includes use of ertugliflozin or a co-crystal or a pharmaceutically acceptable salt thereof, based on the recognition that ertugliflozin is effective for treatment of type 2 diabetes in patients whose eGFR is ≥30 ml/min/1.73 m$^2$ and not in patients whose eGFR is <30 ml/min/1.73 m$^2$; and e) administering ertugliflozin or a co-crystal or a pharmaceutically acceptable salt thereof to the patient.

In one embodiment, the present invention further provides a method of treatment comprising: a) identifying a patient as being in need of treatment for prediabetes, type 1 or type 2 diabetes mellitus; b) determining that the patient's eGFR is ≥30 ml/min/1.73 m$^2$ and <60 ml/min/1.73 m$^2$; c) selecting ertugliflozin as a treatment for the patient based on the recognition that ertugliflozin is effective for treatment of type 2 diabetes mellitus in patients who have an eGFR of 30 ml/min/1.73 m$^2$ but may lack efficacy in patients with eGFR <30 ml/min/1.73 m$^2$; d) administering a pharmaceutical composition comprising ertugliflozin or a co-crystal or a pharmaceutically acceptable salt thereof to the patient; e) determining during treatment with the pharmaceutical composition that the patient's eGFR has dropped below 30 ml/min/1.73 m$^2$; and f) ceasing treatment of the patient with the pharmaceutical composition, based on the recognition that ertugliflozin may lack efficacy in patients with eGFR <30 ml/min/1.73 m$^2$.

In one embodiment, the present invention further provides a method of treatment comprising: a) identifying a patient as being in need of treatment for prediabetes, type 1 or type 2 diabetes mellitus; b) measuring the patient's eGFR; c) determining that the patient's eGFR is ≥30 ml/min/1.73 m$^2$ and <60 ml/min/1.73 m$^2$. d) prescribing a type 2 diabetes treatment for the patient that includes use of ertugliflozin, based on the recognition that ertugliflozin is effective for treatment of type 2 diabetes in patients whose eGFR is ≥30 ml/min/1.73 m$^2$ and not in patients whose eGFR is <30 ml/min/1.73 m$^2$; and e) advising the patient to self-administer ertugliflozin or a co-crystal or a pharmaceutically acceptable salt thereof.

In one embodiment, the present invention further provides a method of treatment comprising: a) identifying a patient as being in need of treatment for prediabetes, type 1 or type 2 diabetes mellitus; b) treating the patient with a first treatment regimen that does not comprise use of ertugliflozin or a co-crystal or a pharmaceutically acceptable salt thereof; c) determining that the first treatment regimen does not provide adequate glycemic control in the patient; d) measuring the patient's eGFR; e) determining that the patient's eGFR is ≥30 ml/min/1.73 m² and <60 ml/min/1.73 m²; f) prescribing an altered treatment regimen for the patient that includes use of ertugliflozin, based on the recognition that ertugliflozin is effective for treatment of prediabetes, type 1 or type 2 diabetes mellitus in patients whose eGFR is ≥30 ml/min/1.73 m² and not in patients whose eGFR is <30 ml/min/1.73 m²; g) advising the patient to administer ertugliflozin or a co-crystal or a pharmaceutically acceptable salt thereof daily as part of the altered treatment regimen; and h) confirming that the patient's glycemic control is improved on the altered treatment regimen, compared to on the first treatment regimen.

In one embodiment, the present invention further provides a method of treatment comprising: a) identifying a patient as being in need of treatment for prediabetes, type 1 or type 2 diabetes mellitus; b) determining that the patient's eGFR is ≥45 ml/min/1.73 m² and <60 ml/min/1.73 m²; c) selecting a type 2 diabetes treatment for the patient that includes ertugliflozin, based on the recognition that ertugliflozin is effective for treatment of prediabetes, type 1 or type 2 diabetes mellitus in patients whose eGFR is ≥45 ml/min/1.73 m² and not in patients whose eGFR is ≤45 ml/min/1.73 m²; and d) administering ertugliflozin or a co-crystal or a pharmaceutically acceptable salt thereof to the patient.

In one embodiment, the present invention further provides a method of treatment comprising: a) identifying a patient as being in need of treatment for prediabetes, type 1 or type 2 diabetes mellitus; b) measuring the patient's eGFR; c) determining that the patient's eGFR is ≥45 ml/min/1.73 m² and <60 ml/min/1.73 m². d) prescribing a prediabetes, type 1 or type 2 diabetes mellitus treatment for the patient that includes use of ertugliflozin, based on the recognition that ertugliflozin is effective for treatment of type 2 diabetes mellitus in patients whose eGFR is ≥45 ml/min/1.73 m² and not in patients whose eGFR is ≤45 ml/min/1.73 m²; and e) administering ertugliflozin or a co-crystal or a pharmaceutically acceptable salt thereof to the patient.

In one embodiment, the present invention further provides a method of treatment comprising: a) identifying a patient as being in need of treatment for prediabetes, type 1 or type 2 diabetes mellitus; b) determining that the patient's eGFR is ≥45 ml/min/1.73 m² and <60 ml/min/1.73 m². c) selecting ertugliflozin as a treatment for the patient based on the recognition that ertugliflozin is effective for treatment of prediabetes, type 1 or type 2 diabetes mellitus in patients who have an eGFR of ≥45 ml/min/1.73 m² but may lack efficacy in patients with eGFR ≤45 ml/min/1.73 m²; d) administering a pharmaceutical composition comprising ertugliflozin or a co-crystal or a pharmaceutically acceptable salt thereof to the patient; e) determining during treatment with the pharmaceutical composition that the patient's eGFR has dropped below 45 ml/min/1.73 m²; and f) ceasing treatment of the patient with the pharmaceutical composition, based on the recognition that ertugliflozin may lack efficacy in patients with eGFR ≤45 ml/min/1.73 m².

In one embodiment, the present invention further provides a method of treatment comprising: a) identifying a patient as being in need of treatment for prediabetes, type 1 or type 2 diabetes mellitus; b) measuring the patient's eGFR; c) determining that the patient's eGFR is ≥45 ml/min/1.73 m² and <60 ml/min/1.73 m². d) prescribing a type 2 diabetes treatment for the patient that includes use of ertugliflozin, based on the recognition that ertugliflozin is effective for treatment of prediabetes, type 1 or type 2 diabetes mellitus in patients whose eGFR is ≥45 ml/min/1.73 m² and not in patients whose eGFR is ≤45 ml/min/1.73 m²; and e) advising the patient to self-administer ertugliflozin or a co-crystal or a pharmaceutically acceptable salt thereof.

In one embodiment, the present invention further provides a method of treatment comprising: a) identifying a patient as being in need of treatment for prediabetes, type 1 or type 2 diabetes mellitus; b) treating the patient with a first treatment regimen that does not comprise use of ertugliflozin; c) determining that the first treatment regimen does not provide adequate glycemic control in the patient; d) measuring the patient's eGFR; e) determining that the patient's eGFR is ≥45 ml/min/1.73 m² and <60 ml/min/1.73 m² f) prescribing an altered treatment regimen for the patient that includes use of ertugliflozin, based on the recognition that ertugliflozin is effective for treatment of prediabetes, type 1 or type 2 diabetes mellitus in patients whose eGFR is ≥45 ml/min/1.73 m² and not in patients whose eGFR is ≤45 ml/min/1.73 m²; g) advising the patient to administer ertugliflozin or a co-crystal or a pharmaceutically acceptable salt thereof daily as part of the altered treatment regimen; and h) confirming that the patient's glycemic control is improved on the altered treatment regimen, compared to on the first treatment regimen.

In one embodiment, in any one of the methods above ertugliflozin or a co-crystal or a pharmaceutically acceptable salt thereof is administered as a pharmaceutical composition, for example a tablet. In one embodiment, the pharmaceutical composition comprises 5 mg or 15 mg of ertugliflozin or a co-crystal or a pharmaceutically acceptable salt thereof. In one embodiment, ertugliflozin is administered once daily.

In one embodiment, the present invention further provides a method of improvement of glycemic control in a patient with prediabetes, type 1 or type 2 diabetes mellitus, wherein the patient's eGFR is ≥30 ml/min/1.73 m² comprising the administration of a pharmaceutical composition comprising ertugliflozin or a co-crystal or a pharmaceutically acceptable salt thereof to the patient. In one embodiment, the patient's eGFR is ≥45 ml/min/1.73 m². In one embodiment, the present invention further provides a method of improvement of glycemic control in a type 2 diabetes mellitus patient with moderate renal impairment comprising the administration of a pharmaceutical composition comprising ertugliflozin or a co-crystal or a pharmaceutically acceptable salt thereof to the patient. In one embodiment, the patient is with moderate A renal (CKD stage 3A) impairment. In one embodiment, the patient is with moderate B renal (CKD stage 3B) impairment. In one embodiment, the pharmaceutical composition comprises 5 mg or 15 mg of ertugliflozin or a co-crystal or a pharmaceutically acceptable salt thereof. In one embodiment, ertugliflozin or a co-crystal or a pharmaceutically acceptable salt thereof is administered once daily.

In one embodiment, the present invention further provides ertugliflozin or a co-crystal or a pharmaceutically acceptable salt thereof for use in the treatment of prediabetes, type 1 or type 2 diabetes mellitus in a patient wherein the patient's eGFR is ≥30 ml/min/1.73 m².

In one embodiment, the present invention further provides a pharmaceutical composition comprising ertugliflozin or a co-crystal or a pharmaceutically acceptable salt thereof for use in the treatment of prediabetes, type 1 or type 2 diabetes mellitus in a patient wherein the patient's eGFR is ≥30 ml/min/1.73 m².

In one embodiment, the present invention further provides ertugliflozin or a co-crystal or a pharmaceutically acceptable salt thereof for use in the improvement of glycemic control in a patient with prediabetes, type 1 or type 2 diabetes mellitus wherein the patient's estimated glomerular filtration rate (eGFR) is ≥30 ml/min/1.73 m².

In one embodiment, the present invention further provides a pharmaceutical composition comprising ertugliflozin or a co-crystal or a pharmaceutically acceptable salt thereof for use in the improvement of glycemic control in a patient with prediabetes, type 1 or type 2 diabetes mellitus wherein the patient's eGFR is ≥30 ml/min/1.73 m².

In one embodiment, in any of the use of ertugliflozin or a co-crystal or a pharmaceutically acceptable salt thereof or a pharmaceutical composition above, the patient's eGFR is ≥30 ml/min/1.73 m² and <90 ml/min/1.73 m². In one embodiment, the patient's eGFR is ≥30 ml/min/1.73 m² and <60 ml/min/1.73 m². In one embodiment, the patient's eGFR is ≥45 ml/min/1.73 m². In one embodiment, the patient's eGFR is ≥45 ml/min/1.73 m² and <90 ml/min/1.73 m². In one embodiment, the patient's eGFR is ≥45 ml/min/1.73 m² and <60 ml/min/1.73 m².

In one embodiment, the present invention further provides ertugliflozin or a co-crystal or a pharmaceutically acceptable salt thereof for use in the treatment of prediabetes, type 1 or type 2 diabetes mellitus in a patient with moderate renal impairment. In one embodiment, the present invention provides a pharmaceutical composition comprising ertugliflozin or a co-crystal or a pharmaceutically acceptable salt thereof for use in the treatment of prediabetes, type 1 or type 2 diabetes mellitus in a patient with moderate renal impairment. In one embodiment, the present invention provides ertugliflozin or a co-crystal or a pharmaceutically acceptable salt thereof for use in the improvement of glycemic control in a prediabetes, type 1 or type 2 diabetes mellitus patient with moderate renal impairment. In one embodiment, the present invention provides a pharmaceutical composition comprising ertugliflozin or a co-crystal or a pharmaceutically acceptable salt thereof for use in the improvement of glycemic control in a prediabetes, type 1 or type 2 diabetes mellitus patient with moderate renal impairment.

In one embodiment, in any use of ertugliflozin or a co-crystal or a pharmaceutically acceptable salt thereof or a pharmaceutical composition above, the patient is with moderate A renal impairment or with moderate B renal impairment. In one embodiment, the use is as an adjunct to diet and exercise. In one embodiment, the patient is an adult patient. In one embodiment, the use is once daily. In one embodiment, the use is 5 mg or 15 mg once daily.

In one aspect of the present invention, in a method or use disclosed herein a patient is patient with type 2 diabetes mellitus (or type 2 diabetes mellitus patient), a patient treated for type 2 diabetes mellitus, a patient diagnosed with type 2 diabetes mellitus or a patient in need of treatment for type 2 diabetes mellitus. In one aspect, a patient is a patient with pre-diabetes.

In a further aspect, the present invention provides a method of improving glycemic control in a patient with type 2 diabetes mellitus, said method comprising a) administering to a patient 5 mg of ertugliflozin or a co-crystal or a pharmaceutically acceptable salt thereof daily, b) determining that the patient requires additional glycemic control and c) administering to the patient 15 mg of ertugliflozin or a co-crystal or a pharmaceutically acceptable salt thereof daily.

In a further aspect of the present invention, in a method or use described herein ertugliflozin or a co-crystal or a pharmaceutically acceptable salt thereof is administered to a patient at a starting dose of 5 mg daily, for example to a patient having an eGFR ≥30 ml/min/1.73 m² or to a patient having an eGFR ≥45 ml/min/1.73 m². In one aspect, in said method or use, the dose is increased to 15 mg daily, for example if the patient requires additional glycemic control. In one aspect, the dose of ertugliflozin or a co-crystal or a pharmaceutically acceptable salt thereof is increased to 15 mg daily in a patient having an eGFR ≥30 ml/min/1.73 m², in a patient having an eGFR ≥45 ml/min/1.73 m² or in a patient having an eGFR ≥60 ml/min/1.73 m².

In a further aspect, the present invention provides a method of improving glycemic control in a patient with type 2 diabetes mellitus, said method comprising a) administering 5 mg of ertugliflozin or a co-crystal or a pharmaceutically acceptable salt thereof daily to a patient having an eGFR ≥30 ml/min/1.73 m² and b) increasing the dose of ertugliflozin or a co-crystal or a pharmaceutically acceptable salt thereof administered to the patient to 15 mg daily in a patient having an eGFR ≥30 ml/min/1.73 m². In one aspect, said patient in step a) requires additional glycemic control.

In a further aspect, the present invention provides a method of improving glycemic control in a patient with type 2 diabetes mellitus, said method comprising a) administering 5 mg of ertugliflozin or a co-crystal or a pharmaceutically acceptable salt thereof daily to a patient having an eGFR ≥30 ml/min/1.73 m², b) determining that the patient has an eGFR ≥30 ml/min/1.73 m² and c) administering 15 mg of ertugliflozin or a co-crystal or a pharmaceutically acceptable salt thereof daily to the patient. In one aspect, step b) further comprises determining that the patient requires additional glycemic control.

In a further aspect, the present invention provides a method of improving glycemic control in a patient with type 2 diabetes mellitus, said method comprising a) administering 5 mg of ertugliflozin or a co-crystal or a pharmaceutically acceptable salt thereof daily to a patient having an eGFR ≥30 ml/min/1.73 m² and b) increasing the dose of ertugliflozin or a co-crystal or a pharmaceutically acceptable salt thereof administered to the patient to 15 mg daily in a patient having an eGFR ≥45 ml/min/1.73 m². In one aspect, said patient in step a) requires additional glycemic control.

In a further aspect, the present invention provides a method of improving glycemic control in a patient with type 2 diabetes mellitus, said method comprising a) administering 5 mg of ertugliflozin or a co-crystal or a pharmaceutically acceptable salt thereof daily to a patient having an eGFR ≥30 ml/min/1.73 m², b) determining that the patient has an eGFR ≥45 ml/min/1.73 m² and c) administering 15 mg of ertugliflozin or a co-crystal or a pharmaceutically acceptable salt thereof daily to the patient. In one aspect, step b) further comprises determining that the patient requires additional glycemic control.

In a further aspect, the present invention provides a method of improving glycemic control in a patient with type 2 diabetes mellitus, said method comprising a) administering 5 mg of ertugliflozin or a co-crystal or a pharmaceutically acceptable salt thereof daily to a patient having an eGFR ≥30 ml/min/1.73 m² and b) increasing the dose of ertugliflozin or a co-crystal or a pharmaceutically acceptable salt thereof administered to the patient to 15 mg daily in a patient having an eGFR ≥60 ml/min/1.73 m². In one aspect, said patient in step a) requires additional glycemic control.

In a further aspect, the present invention provides a method of improving glycemic control in a patient with type 2 diabetes mellitus, said method comprising a) administering 5 mg of ertugliflozin or a co-crystal or a pharmaceutically acceptable salt thereof daily to a patient having an eGFR ≥30 ml/min/1.73 m², b) determining that the patient has an eGFR ≥60 ml/min/1.73 m² and c) administering 15 mg of ertugliflozin or a co-crystal or a pharmaceutically acceptable salt thereof daily to the patient. In one aspect, step b) further comprises determining that the patient requires additional glycemic control.

In a further aspect, the present invention provides a method of improving glycemic control in a patient with type 2 diabetes mellitus, said method comprising a) administering 5 mg of ertugliflozin or a co-crystal or a pharmaceutically acceptable salt thereof daily to a patient having an eGFR ≥45 ml/min/1.73 m² and b) increasing the dose of ertugliflozin or a co-crystal or a pharmaceutically acceptable salt thereof administered to the patient to 25 mg daily in a patient having an eGFR ≥45 ml/min/1.73 m². In one aspect, said patient in step a) requires additional glycemic control.

In a further aspect, the present invention provides a method of improving glycemic control in a patient with type 2 diabetes mellitus, said method comprising a) administering 5 mg of ertugliflozin or a co-crystal or a pharmaceutically acceptable salt thereof daily to a patient having an eGFR ≥45 ml/min/1.73 m², b) determining that the patient has an eGFR ≥45 ml/min/1.73 m² and c) administering 15 mg of ertugliflozin or a co-crystal or a pharmaceutically acceptable salt thereof daily to the patient. In one aspect, step b) further comprises determining that the patient requires additional glycemic control.

In a further aspect, the present invention provides a method of improving glycemic control in a patient with type 2 diabetes mellitus, said method comprising a) administering 5 mg of ertugliflozin or a co-crystal or a pharmaceutically acceptable salt thereof daily to a patient having an eGFR ≥45 ml/min/1.73 m² and b) increasing the dose of ertugliflozin or a co-crystal or a pharmaceutically acceptable salt thereof administered to the patient to 15 mg daily in a patient having an eGFR ≥60 ml/min/1.73 m². In one aspect, said patient in step a) requires additional glycemic control.

In a further aspect, the present invention provides a method of improving glycemic control in a patient with type 2 diabetes mellitus, said method comprising a) administering 5 mg of ertugliflozin or a co-crystal or a pharmaceutically acceptable salt thereof daily to a patient having an eGFR ≥45 ml/min/1.73 m², b) determining that the patient has an eGFR ≥60 ml/min/1.73 m² and c) administering 15 mg of ertugliflozin or a co-crystal or a pharmaceutically acceptable salt thereof daily to the patient. In one aspect, step b) further comprises determining that the patient requires additional glycemic control.

In a further embodiment, in a method or use described herein ertugliflozin or a co-crystal or a pharmaceutically acceptable salt thereof is administered to a patient at a dose of 5 mg daily to a patient having an eGFR ≥60 ml/min/1.73 m² and the patient continues to be administered ertugliflozin or a co-crystal or a pharmaceutically acceptable salt thereof at a dose of 5 mg daily if the patient's eGFR is reduced to 30 to ≤60 ml/min/1.73 m² or to ≥45 to <60 ml/min/1.73 m². Accordingly, in one aspect, the present invention provides a method of improving glycemic control in a patient with type 2 diabetes mellitus, said method comprising a) administering 5 mg of ertugliflozin or a co-crystal or a pharmaceutically acceptable salt thereof daily to a patient having an eGFR ≥60 ml/min/1.73 m², b) determining that the patient has an eGFR ≥30 to <60 ml/min/1.73 m² and c) continuing to administer 5 mg of ertugliflozin or a co-crystal or a pharmaceutically acceptable salt thereof daily to the patient. In an another aspect, the present invention provides a method of improving glycemic control in a patient with type 2 diabetes mellitus, said method comprising a) administering 5 mg of ertugliflozin or a co-crystal or a pharmaceutically acceptable salt thereof daily to a patient having an eGFR ≥60 ml/min/1.73 m², b) determining that the patient has an eGFR>45 to <60 ml/min/1.73 m² and c) continuing to administer 5 mg of ertugliflozin or a co-crystal or a pharmaceutically acceptable salt thereof daily to the patient.

In a further embodiment, in a method or use described herein ertugliflozin or a co-crystal or a pharmaceutically acceptable salt thereof is administered to a patient at a starting dose of 5 mg daily to a patient having an eGFR ≥60 ml/min/1.73 m², the dose of ertugliflozin or a co-crystal or a pharmaceutically acceptable salt thereof is increased to 15 mg daily, for example if the patient requires additional glycemic control, and the dose of ertugliflozin or a co-crystal or a pharmaceutically acceptable salt thereof administered to the patient stays at a dose of 15 mg daily if the patient's eGFR is reduced to 30 to ≤60 ml/min/1.73 m² or to 45 to ≤60 ml/min/1.73 m². Accordingly, in one aspect, the present invention provides a method of improving glycemic control in a patient with type 2 diabetes mellitus, said method comprising a) administering 5 mg of ertugliflozin or a co-crystal or a pharmaceutically acceptable salt thereof daily to a patient having an eGFR ≥60 ml/min/1.73 m², b) increasing the dose of ertugliflozin or a co-crystal or a pharmaceutically acceptable salt thereof administered to the patient to 15 mg daily, for example if the patient requires additional glycemic control, c) determining that the patient has an eGFR ≥30 to <60 ml/min/1.73 m² and d) administering 15 mg of ertugliflozin or a co-crystal or a pharmaceutically acceptable salt thereof daily to the patient. In a further aspect, the present invention provides a method of improving glycemic control in a patient with type 2 diabetes mellitus, said method comprising a) administering 5 mg of ertugliflozin or a co-crystal or a pharmaceutically acceptable salt thereof daily to a patient having an eGFR ≥60 ml/min/1.73 m², b) increasing the dose of ertugliflozin or a co-crystal or a pharmaceutically acceptable salt thereof administered to the patient to 15 mg daily, for example if the patient requires additional glycemic control, c) determining that the patient has an eGFR ≥45 to <60 ml/min/1.73 m² and d) administering 15 mg ertugliflozin or a co-crystal or a pharmaceutically acceptable salt thereof daily to the patient.

In a further embodiment, in a method or use described herein ertugliflozin or a co-crystal or a pharmaceutically acceptable salt thereof is administered to a patient at a starting dose of 5 mg daily to a patient having an eGFR ≥60 ml/min/1.73 m², the dose of ertugliflozin or a co-crystal or a pharmaceutically acceptable salt thereof is increased to 15 mg daily, for example if the patient requires additional glycemic control, and the dose of ertugliflozin or a co-crystal or a pharmaceutically acceptable salt thereof administered to the patient is reduced to a dose of 5 mg daily if the patient's eGFR is reduced to 30 to <60 ml/min/1.73 m² or to ≥45 to <60 ml/min/1.73 m². Accordingly, in one aspect, the present invention provides a method of improving glycemic control in a patient with type 2 diabetes mellitus, said method comprising a) administering 5 mg of ertugliflozin or a co-crystal or a pharmaceutically acceptable salt thereof daily to a patient having an eGFR ≥60 ml/min/1.73 m², b) increasing the dose of ertugliflozin or a co-crystal or a pharmaceutically acceptable salt thereof administered to the patient to 15 mg daily, for example if the patient requires additional glycemic control, c) determining that the patient has an eGFR ≥30 to <60 ml/min/1.73 m² and d) administering 5 mg of ertugliflozin or a co-crystal or a pharmaceutically acceptable salt thereof daily to the patient. In a further aspect, the present invention provides a method of improving glycemic control in a patient with type 2 diabetes mellitus, said method comprising a) administering 5 mg of ertugliflozin or a co-crystal or a pharmaceutically acceptable salt thereof daily to a patient having an eGFR ≥60 ml/min/1.73 m², b) increasing the dose of ertugliflozin or a co-crystal or a pharmaceutically acceptable salt thereof administered to the patient to 15 mg daily, for example if the patient requires additional glycemic control, c) determining that the patient has an eGFR ≥45 to <60 ml/min/1.73 m² and d) administering 10 mg of ertugliflozin or a co-crystal or a pharmaceutically acceptable salt thereof daily to the patient.

In a further embodiment, in a method or use described herein ertugliflozin or a co-crystal or a pharmaceutically acceptable salt thereof is administered to a patient to lower urinary albumin excretion in the patient, wherein the patient has moderate renal impairment or stage 3 chronic kidney disease (CKD).

In a further embodiment, in a method or use described herein ertugliflozin or a co-crystal or a pharmaceutically acceptable salt thereof is administered to a patient who has suffered an ischemic stroke to reduce neuronal damage caused by hyperglycemia following the ischemic stroke.

In a further embodiment, in a method or use described herein ertugliflozin or a co-crystal or a pharmaceutically acceptable salt thereof is administered to a patient who has suffered traumatic brain injury to reduce neuronal damage caused by hyperglycemia following the brain injury.

In a further embodiment, in a method or use described herein ertugliflozin or a co-crystal or a pharmaceutically acceptable salt thereof is administered to a patient who has suffered a closed-head traumatic brain injury to reduce neuronal damage caused by hyperglycemia following the brain injury.

In one aspect, in any one of the methods of uses described above, ertugliflozin or a co-crystal or a pharmaceutically acceptable salt thereof is administered once daily to a patient, i.e. for example 5 mg or 15 mg of ertugliflozin or a co-crystal or a pharmaceutically acceptable salt thereof is administered once daily to a patient.

Another embodiment of the present invention is a pharmaceutical composition for use in the methods described herein comprising a therapeutically effective amount of a compound described herein and a pharmaceutically acceptable excipient, diluent or carrier. The compounds described herein (including the compositions and processes used therein) may also be used in the manufacture of a medicament for the therapeutic applications described herein.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. The compound of the present invention is typically formulated into pharmaceutical dosage forms to provide an easily controllable dosage of the drug and to give the patient an elegant and easily handleable product.

The pharmaceutical compositions also include solvates and hydrates of the compounds of Formula (A) or Formula (B). The term "solvate" refers to a molecular complex of a compound represented by Formula (A) or Formula (B) (including pharmaceutically acceptable salts thereof) with one or more solvent molecules. Such solvent molecules are those commonly used in the pharmaceutical art, which are known to be innocuous to the recipient, e.g., water, ethanol, ethylene glycol, and the like, The term "hydrate" refers to the complex where the solvent molecule is water. The solvates and/or hydrates preferably exist in crystalline form. Other solvents may be used as intermediate solvates in the preparation of more desirable solvates, such as methanol, methyl t-butyl ether, ethyl acetate, methyl acetate, (S)-propylene glycol, (R)-propylene glycol, 1,4-butyne-diol, and the like. The crystalline forms may also exist as complexes with other innocuous small molecules, such as L-phenylalanine, L-proline, L-pyroglutamic acid and the like, as co-crystals or solvates or hydrates of the co-crystalline material. The solvates, hydrates and co-crystalline compounds may be prepared using procedures described in PCT Publication No. WO 08/002824, incorporated herein by reference, or other procedures well-known to those of skill in the art.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided. Suitable pharmaceutical agents that may be used in combination with the compounds of the present invention include anti-obesity agents (including appetite suppressants), anti-diabetic agents, anti-hyperglycemic agents, lipid lowering agents, anti-inflammatory agents and anti-hypertensive agents.

Suitable anti-obesity agents include cannabinoid-1 (CB-1) antagonists (such as rimonabant), 11β-hydroxy steroid dehydrogenase-1 (11β-HSD type 1) inhibitors, stearoyl-CoA desaturase-1 (SCD-1) inhibitor, MCR-4 agonists, cholecystokinin-A (CCK-A) agonists, monoamine reuptake inhibitors (such as sibutramine), sympathomimetic agents, $\beta_3$ adrenergic agonists, dopamine agonists (such as bromocriptine), melanocyte-stimulating hormone analogs, 5HT2c agonists, melanin concentrating hormone antagonists, leptin (the OB protein), leptin analogs, leptin agonists, galanin antagonists, lipase inhibitors (such as tetrahydrolipstatin, i.e. orlistat), anorectic agents (such as a bombesin agonist), neuropeptide-Y antagonists (e.g., NPY Y5 antagonists), $PYY_{3-36}$ (including analogs thereof), thyromimetic agents, dehydroepiandrosterone or an analog thereof, glucocorticoid agonists or antagonists, orexin antagonists, glucagon-like peptide-1 agonists, ciliary neurotrophic factors (such as Axokine™ available from Regeneron Pharmaceuticals, Inc., Tarrytown, N.Y. and Procter & Gamble Company, Cincinnati, Ohio), human agouti-related protein (AGRP) inhibitors, ghrelin antagonists, histamine 3 antagonists or inverse agonists, neuromedin U agonists, MTP/ApoB inhibitors (e.g., gut-selective MTP inhibitors, such as dirlotapide), opioid antagonist, orexin antagonist, and the like.

Preferred anti-obesity agents for use in the combination aspects of the present invention include CB-1 antagonists (e.g., rimonabant, taranabant, surinabant, otenabant, SLV319 (CAS No. 464213-10-3) and AVE1625 (CAS No. 358970-97-5)), gut-selective MTP inhibitors (e.g., dirlotapide, mitratapide and implitapide, R56918 (CAS No. 403987) and CAS No. 913541-47-6), CCKa agonists (e.g., N-benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide described in PCT Publication No. WO 2005/116034 or US Publication No. 2005-0267100 A1), 5HT2c agonists (e.g., lorcaserin), MCR4 agonist (e.g., compounds described in U.S. Pat. No. 6,818,658), lipase inhibitor (e.g., Cetilistat), $PYY_{3-36}$(as used herein "$PYY_{3-36}$" includes analogs, such as peglated $PYY_{3-36}$ e.g., those described in US Publication 2006/0178501), opioid antagonists (e.g., naltrexone), oleoyl-estrone (CAS No. 180003-17-2), obinepitide (TM30338), pramlintide (Symlin®), tesofensine (NS2330), leptin, liraglutide, bromocriptine, orlistat, exenatide (Byetta®), AOD-9604 (CAS No. 221231-10-3) and sibutramine. Preferably, compounds of the present invention and combination therapies are administered in conjunction with exercise and a sensible diet.

Suitable anti-diabetic agents include an acetyl-CoA carboxylase-2 (ACC-2) inhibitor, a phosphodiesterase (PDE)-10 inhibitor, a diacylglycerol acyltransferase (DGAT) 1 or 2 inhibitor, a sulfonylurea (e.g., acetohexamide, chlorpropamide, diabinese, glibenclamide, glipizide, glyburide, glimepiride, gliclazide, glipentide, gliquidone, glisolamide, tolazamide, and tolbutamide), a meglitinide, an α-amylase inhibitor (e.g., tendamistat, trestatin and AL-3688), an α-glucoside hydrolase inhibitor (e.g., acarbose), an α-glucosidase inhibitor (e.g., adiposine, camiglibose, emiglitate, miglitol, voglibose, pradimicin-Q, and salbostatin), a PPARγ agonist (e.g., balaglitazone, ciglitazone, darglitazone, englitazone, isaglitazone, pioglitazone, rosiglitazone and troglitazone), a PPAR α/γ agonist (e.g., CLX-0940, GW-1536, GW-1929, GW-2433, KRP-297, L-796449, LR-90, MK-0767 and SB-219994), a biguanide (e.g., metformin), a glucagon-like peptide 1 (GLP-1) agonist (e.g., exendin-3 and exendin-4), a protein tyrosine phosphatase-1B (PTP-1B) inhibitor (e.g., trodusquemine, hyrtiosal extract, and compounds disclosed by Zhang, S., et al., *Drug Discovery Today*, 12(9/10), 373-381 (2007)), SIRT-1 inhibitor (e.g., reservatrol), a dipeptidyl peptidease IV (DPP-IV) inhibitor (e.g., sitagliptin, vildagliptin, alogliptin and saxagliptin), an insulin secreatagogue, a fatty acid oxidation inhibitor, an A2 antagonist, a c-jun amino-terminal kinase (INK) inhibitor, insulin, an insulin mimetic, a glycogen phosphorylase inhibitor, a VPAC2 receptor agonist and a glucokinase activator. Preferred anti-diabetic agents are metformin and DPP-IV inhibitors (e.g., sitagliptin, vildagliptin, alogliptin and saxagliptin).

In certain embodiments of the methods described herein, ertugliflozin or a co-crystal or a pharmaceutically acceptable salt thereof is administered in combination with sitagliptin and/or metformin. Ertugliflozin or a co-crystal or a pharmaceutically acceptable salt thereof can be administered in the amount of 5 mg or 15 mg while sitagliptin can be administered in the amount of 25 mg or 50 mg. If administered with metformin, metformin can be administered in the amount of 1000 mg or 2000mg. Such combinations (ertugliflozin and sitagliptin or ertugliflozin and metformin) or triple combinations (ertugliflozin, metformin and sitagliptin) can be administered simultaneously or sequentially. Such combinations and triple combinations can be in a single pharmaceutical compositions or each pharmaceutical agent can be in a separate pharmaceutical composition.

Suitable anti-inflammatory agents include genital tract/urinary tract infection preventatives and treatments. Exemplary agents include cranberries (i.e. *Vaccinium macrocarpon*) and cranberry derivatives such as cranberry juice, cranberry extracts or flavonols of cranberries. Cranberry extracts may include one or more flavonols (i.e. anthocyanins and proanthocyanidins) or a purified cranberry flavonol compound, including myricetin-3-β-xylopyranoside, quercetin-3-β-glucoside, quercetin-3-α-arabinopyranoside, 3'-methoxyquercetin-3-α-xylopyranoside, quercetin-3-O-(6"-p-coumaroyl)-β-galactoside, quercetin-3-O-(6"-benzoyl)-β-galactoside, and/or quercetin-3-α-arabinofuranoside.

Embodiments of the present invention are illustrated by the following Example. It is to be understood, however, that the embodiments of the invention are not limited to the specific details of the Example, as other variations thereof will be known, or apparent in light of the instant disclosure, to one of ordinary skill in the art.

EXAMPLES

Results of a Phase I, Single Dose Study to Study The Effect of Renal Impairment on the Pharmacokinetics and Pharmacodynamics of Ertugliflozin in Subjects with Type 2 Diabetes Mellitus (T2DM)

Background and aims: Ertugliflozin is a highly selective and potent inhibitor of Sodium Glucose co-Transporter 2 (SGLT2) that is under development for the treatment of T2DM. Ertugliflozin inhibits renal glucose reabsorption resulting in urinary glucose excretion, thereby reducing plasma glucose and HbA1c. The glycemic efficacy of SGLT2 inhibitors depends on the amount of glucose filtered through the kidney and the kidney is potentially a site of ertugliflozin metabolism. As renal impairment (RI) is a co-morbidity of T2DM, this study evaluated the effect of RI on the pharmacokinetics, pharmacodynamics (as measured by 24-hour urinary glucose excretion [UGE24]), safety, and tolerability of ertugliflozin in subjects with T2DM.

Materials and methods: In this Phase 1, multi-center, open-label study, a single 15 mg oral dose of ertugliflozin was administered in the fasted state to healthy and T2DM subjects with normal renal function (estimated glomerular filtration rate [eGFR]≥90 mL/min) and in T2DM subjects with mild RI (eGFR 60-89 mL/min), moderate RI (eGFR 30-59 mL/min) and severe RI (eGFR <30 mL/min). Serial blood samples and urine samples at specified intervals were collected for 96 hours post-dose for pharmacokinetic evaluation and for measurement of UGE24.

Results: Geometric mean (CV %) values for ertugliflozin exposure parameters (area under the concentration-time curve [$AUC_{0-inf}$] and peak concentration [$C_{max}$]) and change from baseline in UGE24 are presented in the table below. Ertugliflozin exposures were similar in healthy subjects and T2DM subjects with normal renal function. Based on an analysis of variance, the geometric mean ratio (GMR) [90% confidence interval (CI)] for $AUC_{0-inf}$ in T2DM subjects with mild, moderate, and severe RI compared to healthy and T2DM subjects with normal renal function (pooled) was 1.56 [1.28, 1.91], 1.70 [1.39, 2.08], and 1.55 [1.24, 1.94], respectively. The mean GMR [90% CI] for change from baseline in UGE24 was 0.50 [0.27, 0.91], 0.38 [0.21, 0.70], and 0.14 [0.07, 0.27] in T2DM subjects with mild, moderate, and severe RI, respectively, compared to T2DM subjects with normal renal function.

Conclusion: Renal insufficiency moderately increased systemic exposure of ertugliflozin compared to subjects with normal renal function. Despite the higher ertugliflozin exposure, UGE24 decreased with declining renal function and a subsequent decrease in the filtered glucose load. A single 15 mg dose of ertugliflozin was well tolerated in subjects with normal renal function and in T2DM subjects with renal impairment.

| Renal Function | $C_{max}$ (ng/mL) | $AUC_{0-inf}$ (ng · hour/mL) | Change from baseline in UGE24 (g) |
|---|---|---|---|
| Healthy Normal | 219 | 1236 | 46.3 |
| (n = 8) | (26) | (27) | (31) |
| T2DM Normal | 216 | 1199 | 72.3 |
| (n = 6) | (35) | (42) | (30) |
| T2DM Mild RI | 313 | 1908 | 36.0 |
| (n = 8) | (30) | (28) | (113) |
| T2DM Moderate RI | 306 | 2075 | 27.6 |
| (n = 8) | (23) | (19) | (68) |
| T2DM Severe RI | 196 | 1895 | 10.1 |
| (n = 6) | (28) | (23) | (57) |

Note:
Values presented are geometric mean (% CV)

Protocol for a Phase 3 Study of the Efficacy and Safety of Ertugliflozin in Participants with Type 2 Diabetes Mellitus with Stage 3 Chronic Kidney Disease who have Inadequate Glycemic Control on Antihyperglycemic Therapy This study will evaluate the efficacy and safety of ertugliflozin (MK-8835/PF-04971729) in participants with type 2 diabetes mellitus with Stage 3 Chronic Kidney Disease (CKD) who have inadequate glycemic control on background antihyperglycemic therapy. The duration of this trial will be up to 67 weeks. This will consist of a 1-week Screening Period, a 10-week wash-off period from metformin, if needed, and a 2-week placebo run-in period, a 52-week double-blind treatment period, and a 14-day post-treatment follow-up period. The primary objective of this trial is to assess the A1C-lowering efficacy of the addition of ertugliflozin compared to the addition of placebo with an underlying hypothesis that addition of treatment with ertugliflozin provides greater reduction in A1C compared to the addition of placebo; the primary objective will be tested for both 5-mg and 15-mg doses of ertugliflozin.

Condition: Type 2 Diabetes Mellitus
Intervention: Drug: Ertugliflozin; Drug: Placebo
Phase: Phase 3
Study Type: Interventional
Study Design: Allocation: Randomized
Endpoint Classification: Safety/Efficacy Study
Intervention Model: Parallel Assignment
Masking: Double Blind (Subject, Investigator)
Primary Purpose: Treatment
Official Title: A Phase III, Multicenter, Randomized, Double-Blind, Placebo-Controlled Clinical Trial to Evaluate the Efficacy and Safety of Ertugliflozin (MK-8835/PF-04971729) in Subjects With Type 2 Diabetes Mellitus With Stage 3 Chronic Kidney Disease Who Have Inadequate Glycemic Control on Background Antihyperglycemic Therapy
Primary Outcome Measures:
  Change from Baseline in A1C at Week 26 Overall cohort of Stage 3 CKD, estimated glomerular filtration rate (eGFR) of ≥30 to <60 mL/min/1.73 m²
  Number of Participants Who Experienced an Adverse Event (AE)
  Number of Participants Who Discontinued Study Treatment due to an AE Secondary Outcome Measures:
  Change from Baseline in A1C at Week 26 Cohort of Stage 3A CKD, eGFR of ≥45 to <60 mL/min/1.73 m2
  Change from Baseline in Body Weight at Week 26 Cohort of Stage 3A CKD, eGFR of ≥45 to <60 mL/min/1.73 m2
  Change from Baseline in Systolic Blood Pressure at Week 26 Cohort of Stage 3A CKD, eGFR of ≥45 to <60 mL/min/1.73 m2
  Change from Baseline in Fasting Plasma Glucose at Week 26 Cohort of Stage 3A CKD, eGFR of ≥45 to <60 mL/min/1.73 m2
  Number of Participants with an A1C of <7% (53 mmol/mol) at Week 26 Cohort of Stage 3A CKD, eGFR of ≥45 to <60 mL/min/1.73 m2
Arms
Ertugliflozin, 5 mg, oral, one 5 mg ertugliflozin tablet and one placebo tablet, once daily for 52 weeks Drug: Ertugliflozin
Ertugliflozin, 15 mg, oral, one 5 mg and one 10 mg tablet, once daily for 52 weeks Drug: Ertugliflozin
Matching placebo Drug: Placebo, oral, tablet, 10 mg or 5 mg and 10 mg tablet once daily for 52 weeks
Eligibility
Ages Eligible for Study: 25 Years and older
Genders Eligible for Study: Both
Accepts Healthy Volunteers: No
Inclusion Criteria:
  Diagnosis of T2DM
  On stable diabetes therapy (diet/exercise therapy alone or anti-hyperglycemic agents [AHA] monotherapy or combination therapy) for at least 6 weeks prior to study participation OR on metformin (with or without diet/exercise therapy or other AHA therapy) and is willing to undergo a 10-week metformin wash-off period
  Body Mass Index (BMI) greater than or equal to 18.0 kg/m^2
  Male, postmenopausal female or surgically sterile female
  If a female of reproductive potential, agrees to remain abstinent or to use (or have their partner use) 2 acceptable combinations of birth control while participating in the trial and for 14 days after the last use of study drug.

Exclusion Criteria:
- History of type 1 diabetes mellitus or a history of ketoacidosis
- History of other specific types of diabetes (e.g., genetic syndromes, secondary pancreatic diabetes, diabetes due to endocrine disorders, drug—or chemical-induced, and post-organ transplant)
- History of nephrotic range proteinuria with hypoalbuminemia and edema
- History of rapidly progressive glomerulonephritis, lupus nephritis, renal or systemic vasculitis, renal artery stenosis with renovascular hypertension, or ischemic nephropathy
- History of familial renal glucosuria
- History of renal dialysis or renal transplant or renal disease requiring treatment with any immunosuppressive agent
- A known hypersensitivity or intolerance to any (sodium-glucose co-transporter 2) SGLT2 inhibitor
- On a weight-loss program or weight-loss medication or other medication associated with weight changes and is not weight stable
- Has undergone bariatric surgery within the past 12 months
- Has been treated with rosiglitazone or other SGLT2 inhibitors within 12 weeks of study participation
- Has active, obstructive uropathy or indwelling urinary catheter
- History of myocardial infarction, unstable angina, arterial revascularization, stroke, transient ischemic attack, or New York Heart Association (NYHA) functional class III-IV heart failure within 3 months of study participation
- A history of malignancy ≤5 years prior to study participation, except for adequately treated basal or squamous cell skin cancer or in situ cervical cancer
- Known history of Human Immunodeficiency Virus (HIV)
- Has blood dyscrasias or any disorders causing hemolysis or unstable red blood cells or any other clinically significant hematological disorder (such as aplastic anemia, myeloproliferative or myelodysplastic syndromes, thrombocytopenia)
- A medical history of active liver disease (other than non-alcoholic hepatic steatosis), including chronic active hepatitis B or C, primary biliary cirrhosis, or active symptomatic gallbladder disease
- Has any clinically significant malabsorption condition
- If taking thyroid replacement therapy, has not been on a stable dose for at least 6 weeks prior to study participation
- Has been previously randomized in a study with ertugliflozin
- Has participated in other studies involving an investigational drug within 30 days prior or during study participation
- Has undergone a surgical procedure within 6 weeks prior to or during study participation
- Has a positive urine pregnancy test
- Is pregnant or breast-feeding, or is planning to conceive during the trial, including 14 days following the last dose of study medication
- Planning to undergo hormonal therapy in preparation to donate eggs during the trial, including 14 days following the last dose of study medication
- Excessive consumption of alcoholic beverages or binge drinking
- Has donated blood or blood products within 6 weeks of study participation or plans to donate blood or blood products at any time during the trial Throughout this application, various publications are referenced. The disclosures of these publications in their entireties are hereby incorporated by reference into this application for all purposes.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification including the examples be considered as exemplary only, with a true scope and spirit of the invention being indicated by the following claims.

What is claimed is:

1. A method of treating prediabetes, type 1 or type 2 diabetes mellitus in a patient in need thereof comprising administering ertugliflozin or a co-crystal or a pharmaceutically acceptable salt thereof to the patient, wherein the patient has moderate renal impairment or stage 3 chronic kidney disease (CKD).

2. The method of claim 1, wherein the patient has moderate A renal impairment or stage 3A chronic kidney disease (CKD).

3. The method of claim 1, wherein the patient has moderate B renal impairment or stage 3B chronic kidney disease (CKD).

4. A method for improving glycemic control in a patient with type 2 diabetes comprising administering ertugliflozin or a co-crystal or a pharmaceutically acceptable salt thereof to the patient, wherein the patient has moderate renal impairment or stage 3 chronic kidney disease (CKD).

5. The method of claim 4, wherein the patient has moderate A renal impairment or stage 3A chronic kidney disease (CKD).

6. The method of claim 4, wherein the patient has moderate B renal impairment or stage 3B chronic kidney disease (CKD).

7. The method of claim 1, wherein ertugliflozin or a co-crystal or a pharmaceutically acceptable salt thereof is administered as a pharmaceutical composition.

8. The method of claim 1, wherein ertugliflozin or a co-crystal or a pharmaceutically acceptable salt thereof is administered in the amount of 5 mg or 15 mg of ertugliflozin.

9. The method of claim 1, wherein ertugliflozin or a co-crystal or a pharmaceutically acceptable salt thereof is administered once daily.

10. The method of claim 1, wherein ertugliflozin or a co-crystal or a pharmaceutically acceptable salt thereof is administered with at least one additional pharmaceutical agent.

11. The method of claim 10, wherein ertugliflozin or a co-crystal or a pharmaceutically acceptable salt thereof is administered with sitagliptin or a pharmaceutically acceptable salt thereof.

12. The method of claim 11, wherein the sitagliptin or pharmaceutically acceptable salt thereof is in the amount of 25 mg or 50 mg.

13. The method of claim 1, wherein the method results in deceased blood pressure and decreased uric acid.

* * * * *

UNITED STATES PATENT AND TRADEMARK OFFICE
CERTIFICATE OF CORRECTION

PATENT NO. : 10,285,973 B2
APPLICATION NO. : 15/523512
DATED : May 14, 2019
INVENTOR(S) : Ramachandra G. Naik et al.

It is certified that error appears in the above-identified patent and that said Letters Patent is hereby corrected as shown below:

In the Claims

Column 42 Claim 13, Line 64, appears as follows:
"deceased blood pressure and decreased uric acid."

Should appear as follows:
"decreased blood pressure and decreased uric acid."

Signed and Sealed this
Twenty-seventh Day of October, 2020

Andrei Iancu
*Director of the United States Patent and Trademark Office*